US010485769B2

(12) United States Patent
Kaur et al.

(10) Patent No.: US 10,485,769 B2
(45) Date of Patent: Nov. 26, 2019

(54) CHOLESTERYL ESTER TRANSFER PROTEIN (CETP) INHIBITION IN THE TREATMENT OF CANCER

(71) Applicant: KING ABDULLAH UNIVERSITY OF SCIENCE AND TECHNOLOGY, Thuwal (SA)

(72) Inventors: Mandeep Kaur, Thuwal (SA); Luke E. Esau, Cape Town (ZA); Sunil Sagar, Thuwal (SA)

(73) Assignee: King Abdullah University of Science and Technology, Thuwal (SA)

(*) Notice: Subject to any disclaimer, the term of this patent is extended or adjusted under 35 U.S.C. 154(b) by 0 days.

(21) Appl. No.: 15/549,496

(22) PCT Filed: Feb. 23, 2016

(86) PCT No.: PCT/IB2016/050987
§ 371 (c)(1),
(2) Date: Aug. 8, 2017

(87) PCT Pub. No.: WO2016/135633
PCT Pub. Date: Sep. 1, 2016

(65) Prior Publication Data
US 2018/0049997 A1 Feb. 22, 2018

Related U.S. Application Data

(60) Provisional application No. 62/120,100, filed on Feb. 24, 2015.

(51) Int. Cl.
A61K 31/122 (2006.01)
C12N 15/113 (2010.01)
(Continued)

(52) U.S. Cl.
CPC .......... A61K 31/122 (2013.01); A61K 31/138 (2013.01); A61K 31/22 (2013.01);
(Continued)

(58) Field of Classification Search
CPC .. A61K 31/122; A61K 31/405; A61K 31/517; A61K 31/565; C12N 15/113;
(Continued)

(56) References Cited

U.S. PATENT DOCUMENTS 9,890,106 B2 * 2/2018 Sagar ..................... A61K 31/05
2005/0171040 A1 8/2005 Polisky et al.
(Continued)

FOREIGN PATENT DOCUMENTS

WO 2003014306 A2 2/2003
WO 2004052920 A2 6/2004
(Continued)

OTHER PUBLICATIONS

Ahmad (Plumbagin-induced Apoptosis of Human Breast Cancer Cells is Mediated by Inactivation of NF—κB and Bcl-2, Journal of Cellular Biochemistry, 2008, 105, pp. 1461-1461).*
(Continued)

Primary Examiner — Savitha M Rao
(74) Attorney, Agent, or Firm — Pabst Patent Group LLP

(57) ABSTRACT

In one embodiment, the invention provides methods of treatment which use therapeutically effective amounts of Cholesteryl Ester Transfer Protein (CETP) inhibitors to treat a variety of cancers. In certain embodiments, the inhibitor is a CETP-inhibiting small molecule, CETP-inhibiting antisense oligonucleotide, CETP-inhibiting siRNA or a CETP-inhibiting antibody. Related pharmaceutical compositions, kits, diagnostics and screens are also provided.

9 Claims, 16 Drawing Sheets

(51) Int. Cl.
- *A61K 31/138* (2006.01)
- *A61K 31/22* (2006.01)
- *A61K 31/366* (2006.01)
- *A61K 31/40* (2006.01)
- *A61K 31/405* (2006.01)
- *A61K 31/4418* (2006.01)
- *A61K 31/47* (2006.01)
- *A61K 31/505* (2006.01)
- *A61K 31/506* (2006.01)
- *A61K 31/517* (2006.01)
- *A61K 31/565* (2006.01)
- *G01N 33/50* (2006.01)
- *G01N 33/574* (2006.01)
- *A61P 35/00* (2006.01)

(52) U.S. Cl.
CPC ............ *A61K 31/366* (2013.01); *A61K 31/40* (2013.01); *A61K 31/405* (2013.01); *A61K 31/4418* (2013.01); *A61K 31/47* (2013.01); *A61K 31/505* (2013.01); *A61K 31/506* (2013.01); *A61K 31/517* (2013.01); *A61K 31/565* (2013.01); *A61P 35/00* (2018.01); *C12N 15/113* (2013.01); *G01N 33/5011* (2013.01); *G01N 33/57415* (2013.01); *C12N 2310/11* (2013.01); *C12N 2310/14* (2013.01); *G01N 2800/52* (2013.01)

(58) Field of Classification Search
CPC ............ C12N 2310/11; C12N 2310/14; G01N 2800/52; G01N 33/5011; G01N 33/57415
See application file for complete search history.

(56) References Cited

U.S. PATENT DOCUMENTS

2010/0179145 A1* 7/2010 Gallagher ............ A61K 31/403
                       514/235.2
2013/0219528 A1* 8/2013 Borgstrom ............ A61K 31/05
                       800/3

FOREIGN PATENT DOCUMENTS

| WO | 2012154944 A2 | 11/2012 |
| WO | 2013164683 A1 | 11/2013 |
| WO | 2014143031 A1 | 9/2014 |

OTHER PUBLICATIONS

Tokunaga (Cytotoxic Antifeedant from Dionaea muscipula Ellis: A Defensive Mechanism of Carnivorous Plants against Predators, 2004, Bull Chem Soc Jpn, 77, pp. 537-541).*

Sagar et al. (Anti-cancer agents in Medicinal chemistry, 2014, 14, pp. 170-180).*

* cited by examiner (C)

| Study Group | Total Cholesterol/HDL | HDL/LDL |
|---|---|---|
| Reference | 1.38 | 3.0 |
| Vehicle | 1.40 | 3.4 |
| 5 mg/ml AP | 1.40 | 3.1 |
| 2 mg/kg PL | 1.30 | 1.8 |

Figure 6 (Cont'd)

CHOLESTERYL ESTER TRANSFER PROTEIN (CETP) INHIBITION IN THE TREATMENT OF CANCER

RELATED APPLICATIONS

This application is a United States national phase patent application based upon and claiming priority from international patent application number PCT/IB2016/050987 filed Feb. 23, 2016, which claims the benefit of priority of U.S. provisional application No. 62/120,100, filed Feb. 24, 2015, entitled "Cholesteryl Ester Transfer Protein (CETP) Inhibition in the Treatment of Cancer", the entire contents of which two applications are incorporated by reference herein.

FIELD OF THE INVENTION

In one embodiment, the invention provides methods of treatment which use therapeutically effective amounts of Cholesteryl Ester Transfer Protein (CETP) inhibitors to treat a variety of cancers. In certain embodiments, the inhibitor is a CETP-inhibiting small molecule, CETP-inhibiting antisense oligonucleotide, CETP-inhibiting siRNA or a CETP-inhibiting antibody.

Related pharmaceutical compositions, kits, diagnostics and screens are also provided.

BACKGROUND OF THE INVENTION

The majority of breast cancers occur in postmenopausal women, with 75% of these tumors being estrogen dependent as defined as estrogen receptor (ER) positive. Tamoxifen, an anti-estrogen, has been the mainstay of treatment for hormone-dependent breast cancers. However, recent clinical trials have shown that inhibitors of aromatase, which catalyze the rate-limiting step of estrogen biosynthesis, may be more effective than tamoxifen in treating hormone-dependent breast cancers in postmenopausal women. Unfortunately, resistance to both these endocrine therapies is inevitable in metastatic breast cancer.

We have screened derivatives of plumbagin (5-hydroxy-2-methyl-1, 4-naphthoquinone) against various human cancer cell lines and we have determined that a derivative acetyl plumbagin ("AP") is active in breast cancer cell lines models. Further, we have shown that AP has several advantages over Tamoxifen in these cell line models. See U.S. Patent Application Document No. 20140107196, which is incorporated herein in its entirety.

There remains a compelling need to develop more effective therapies for breast cancer patients, particularly those with acquired anti-estrogen resistance, in addition to those with intrinsic resistance to anti-estrogen and anti-HER2 therapies.

SUMMARY OF THE INVENTION

In one embodiment, the invention provides a method of treating a subject who suffers from a cancer, the method comprising administering to the subject a therapeutically effective amount of one or more compositions selected from the group consisting of a Cholesteryl Ester Transfer Protein (CETP) inhibiting small molecule as described hereinafter, a CETP inhibiting antisense oligonucleotide, a CETP inhibiting siRNA and a CTEP inhibiting antibody.

In another embodiment, the survival time of a patient suffering from breast cancer is increased by concomitant administration of a CETP inhibitor and one or more additional anticancer agents selected from the group consisting of tamoxifen, paclitaxel and fluorouracil (5-FU). In some embodiments, the subject is co-administered plumbagin (5-hydroxy-2-methyl-1,4-naphthoquinone), or an analog, derivative, pharmaceutically acceptable salt, enantiomer, diastereomer, solvate or polymorph thereof. Methods of treatment of the invention are particularly useful in the treatment of a patient who suffers from a form of refractory breast cancer, who has developed an acquired anti-estrogen resistance or who exhibits an intrinsic resistance to anti-estrogen and anti-HER2 therapies.

In still other embodiments, the invention provides a method of predicting the responsiveness of a patient suffering from a cancer to treatment with one or more anticancer agents selected from the group consisting of tamoxifen, paclitaxel and fluorouracil (5-FU), the method comprising measuring levels of CETP in a sample taken from the patient and comparing measured values to control CETP values of a healthy subject, wherein decreased survival times are predicted where measured CETP levels exceed control levels. Preferably, the measured CETP levels are often mRNA levels of CETP in cancer cells or plasma CETP levels.

The invention also provides a method of determining whether a composition is effective in the treatment of one or more cancers, the method comprising:
(a) contacting a cancer cell sample with the composition;
(b) measuring at least one cancer cell sample indicator selected from the group consisting of cellular viability, cancer cell levels of mitochondrial outer membrane potential (MOMP) and cellular levels of apoptosis-associated proteins; and
(c) comparing measured cancer cell sample viability, MOMP levels and/or levels of apoptosis-associated proteins with cell viability, MOMP levels and/or levels of apoptosis-associated proteins in a control cancer cell sample which is contacted with plumbagin (5-hydroxy-2-methyl-1,4-naphthoquinone), or an analog, derivative, pharmaceutically acceptable salt, enantiomer, diastereomer, solvate or polymorph thereof;
wherein the composition is determined to be effective in the treatment of one or more cancers if measured levels of cell viability, MOMP and/or apoptosis-associated proteins are approximately the same as or less than comparable control levels.

Another screening method of the invention involves determining whether a composition is effective in the treatment of one or more cancers, the method comprising:
(a) contacting a cancer cell sample with the composition;
(b) measuring cellular Cholesteryl Ester Transfer Protein (CETP) levels; and
(c) comparing measured cancer cell CETP levels with CTEP levels of a control cancer cell sample which is contacted with plumbagin (5-hydroxy-2-methyl-1,4-naphthoquinone), or an analog, derivative, pharmaceutically acceptable salt, enantiomer, diastereomer, solvate or polymorph thereof;
wherein the composition is determined to be effective in the treatment of one or more cancers if measured CTEP levels are approximately the same as or less than comparable control levels.

Significantly, we have discovered that acetyl plumbagin (AP) and related derivatives are CETP-inhibitors that, like other CETP inhibitors such as those described hereinafter, can be combined with Tamoxifen to increase the viability of normal cells and significantly decrease the viability of cancer cells. CETP inhibitor co-therapy protects normal cells from toxic effects of Tamoxifen and enables tamoxifen to kill cancer cells at half of the normal recommended dose.

DETAILED DESCRIPTION OF THE INVENTION

Figure 1:
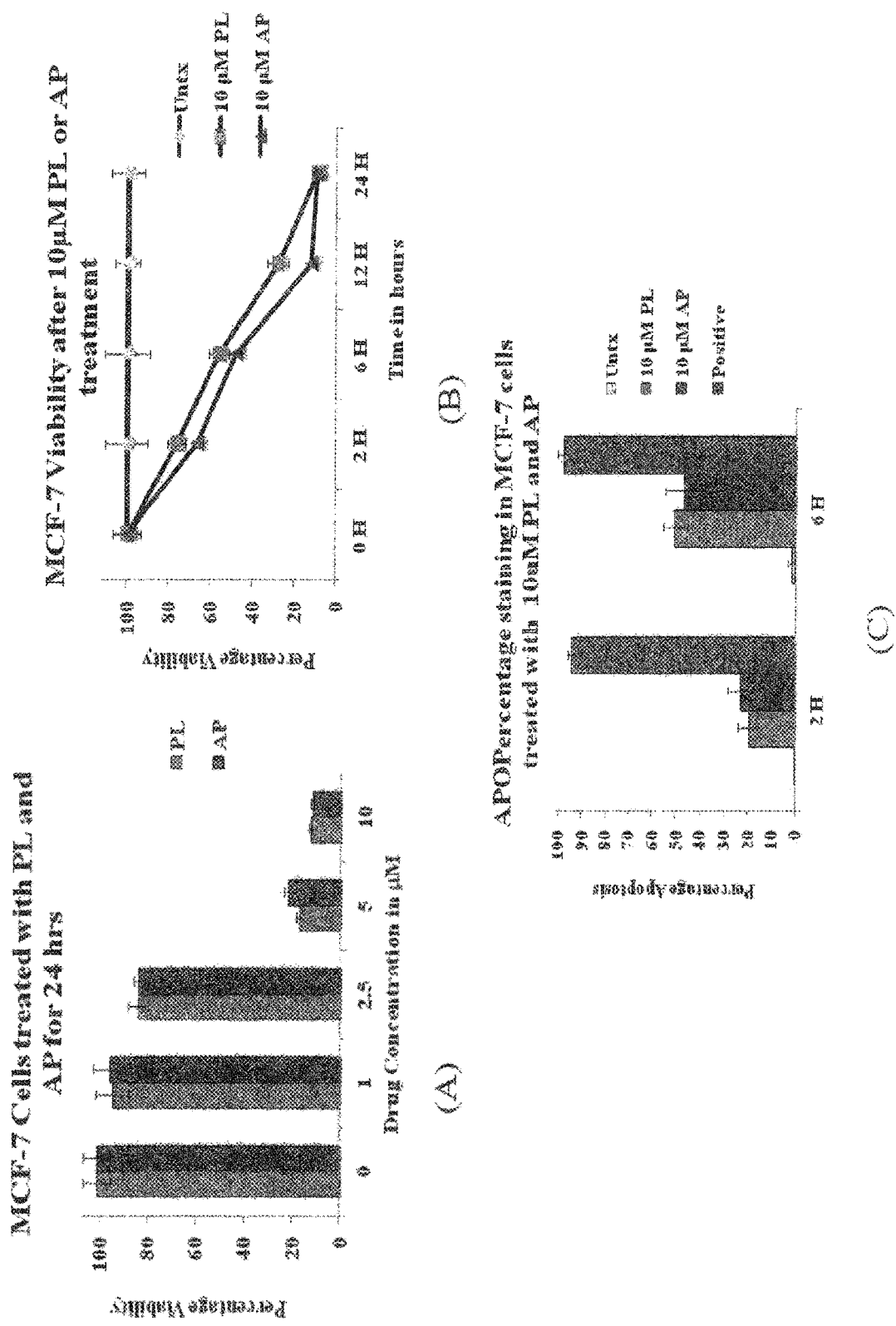
FIG. 1: MTT and APOPercentage assays to assess the differential cytotoxicity and apoptosis inducing potential of AP and PL in MCF-7 cells. Viability was determined using MTT assay after incubating the MCF-7 cells with different concentrations of AP and PL (A), at different time-points (B). The apoptosis inducing potential of 10 µM AP and PL in MCF-7 was determined by using APOPercentage assay performed at intervals of 2 and 6 h.

In accordance with the present invention there may be employed conventional chemical synthetic methods and other biological and pharmaceutical techniques within the skill of the art. Such techniques are well-known and are otherwise explained fully in the literature.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It is to be noted that as used herein and in the appended claims, the singular forms "a," "and" and "the" include plural references unless the context clearly dictates otherwise.

Furthermore, the following terms shall have the definitions set out below. It is understood that in the event a specific term is not defined herein below, that term shall have a meaning within its typical use within context by those of ordinary skill in the art.

The term "compound", as used herein, unless otherwise indicated, refers to any specific chemical compound disclosed herein. Within its use in context, the term generally refers to a single compound comprising a hydrophobic moiety and a linker which is capable of reacting and forming a covalent bond with a fusion protein as otherwise described herein. In certain instances the term may also refer to stereoisomers and/or optical isomers (including racemic mixtures) or enantiomerically enriched mixtures of disclosed compounds. Compounds which are disclosed are those which are stable and where a choice of substituents and claim elements is available, the substituent or claim element is chosen such that stable compounds are formed from the disclosed elements and substituents. The symbol ----- in a chemical structure or formula signifies that either a double or single bond may be present between the atoms to which such symbol is attached, depending upon the valence of those atoms and substituents which are on such atoms.

The term "patient" or "subject" is used throughout the specification within context to describe an animal, especially including a domesticated mammal and preferably a human, to whom a treatment or procedure, including a prophylactic treatment or procedure is performed. For treatment of those infections, conditions or disease states which are specific for a specific animal such as a human patient, the term patient refers to that specific animal. In most instances, the patient or subject of the present invention is a domesticated/agricultural animal or human patient of either or both genders.

The term "effective" is used herein, unless otherwise indicated, to describe an amount of a compound or composition which, in context, is used to produce or effect an intended result, whether that result relates to the treatment of a cancer in a patient or subject. The term effective subsumes all other effective amount or effective concentration terms which are otherwise described or used in the present application.

"Hydrocarbon" or "hydrocarbyl" refers to any monovalent (or divalent in the case of alkylene groups) radical containing carbon and hydrogen, which may be straight, branch-chained or cyclic in nature. Hydrocarbons include linear, branched and cyclic hydrocarbons, including alkyl groups, alkylene groups, saturated and unsaturated hydrocarbon groups including aromatic groups both substituted and unsubstituted, alkene groups (containing double bonds between two carbon atoms) and alkyne groups (containing triple bonds between two carbon atoms). In certain instances, the terms substituted alkyl and alkylene are sometimes used synonymously.

"Alkyl" refers to a fully saturated monovalent radical containing carbon and hydrogen, and which may be cyclic, branched or a straight chain. Examples of alkyl groups are methyl, ethyl, n-butyl, n-hexyl, n-heptyl, n-octyl, n-nonyl, n-decyl, isopropyl, 2-methyl-propyl, cyclopropyl, cyclopropylmethyl, cyclobutyl, cyclopentyl, cyclopentylethyl, cyclohexylethyl and cyclohexyl. Preferred alkyl groups are $C_1$-$C_6$ alkyl groups. "Alkylene" refers to a fully saturated hydrocarbon which is divalent (may be linear, branched or cyclic) and which is optionally substituted. Preferred alkylene groups are $C_1$-$C_6$ alkylene groups. Other terms used to indicate substituent groups in compounds according to the present invention are as conventionally used in the art.

The term "aryl" or "aromatic", in context, refers to a substituted or unsubstituted monovalent aromatic radical having a single ring (e.g., benzene or phenyl). Other examples of aryl groups, in context, may include heterocyclic aromatic ring systems "heteroaryl" groups having one or more nitrogen, oxygen, or sulfur atoms in the ring (5- or 6-membered heterocyclic rings) such as imidazole, furyl, pyrrole, pyridyl, furanyl, thiene, thiazole, pyridine, pyrimidine, pyrazine, triazole, oxazole, among others, which may be substituted or unsubstituted as otherwise described herein.

The term "heterocyclic group" "heterocycle" as used throughout the present specification refers to an aromatic ("heteroaryl") or non-aromatic cyclic group forming the cyclic ring and including at least one and up to three hetero atoms such as nitrogen, sulfur or oxygen among the atoms forming the cyclic ring. The heterocyclic ring may be saturated (heterocyclic) or unsaturated (heteroaryl). Exemplary heterocyclic groups include, for example pyrrolidinyl, piperidinyl, morpholinyl, pyrrole, pyridine, pyridone, pyrimidine, imidazole, thiophene, furan, pyran, thiazole, more preferably pyrimidinyl, pyrrolidinyl, piperidinyl, morpholinyl, oxazole, isoxazole, pyrrole, pyridine, thiophene, thiazole and even more preferably pyrimidinyl, especially uracil or cytosine which are optionally substituted, furyl, 3-methylfuryl, thiazole, piperazinyl, N-methylpiperazinyl, tetrahydropyranyl and 1,4-dioxane, among others. Additional heterocyclic groups include oxazole, benzoxazole, pyrrole, dihydropyrrole, benzopyrrole, benzodihydropyrrole, indole, indolizine, among others.

Exemplary heteroaryl moieties which may be used in the present invention include for example, pyrrole, pyridine, pyridone, pyridazine, pyrimidine, pyrazine, pyrazole, imidazole, triazole, tetrazole, oxadiazole, sulfur-containing aromatic heterocycles such as thiophene; oxygen-containing aromatic heterocycles such as furan and pyran, and including aromatic heterocycles comprising 2 or more hetero atoms selected from among nitrogen, sulfur and oxygen, such as thiazole, thiadiazole, isothiazole, isoxazole, furazan and oxazole. Further heteroaryl groups may include pyridine, triazine, pyridone, pyrimidine, imidazole, furan, pyran, thiazole. Pyrimidine groups, especially uracil and cytosine, optionally substituted, are preferred.

The term "substituted" shall mean substituted at a carbon (or nitrogen) position within context, hydroxyl, carboxyl, cyano (C≡N), nitro ($NO_2$), halogen (preferably, 1, 2 or 3 halogens, especially on an alkyl, especially a methyl group such as a trifluoromethyl), alkyl group (preferably, $C_1$-$C_{10}$, more preferably, $C_1$-$C_6$), alkoxy group (preferably, $C_1$-$C_6$ alkyl or aryl, including phenyl and substituted phenyl), ester (preferably, $C_1$-$C_6$ alkyl or aryl) including alkylene. ester (such that attachment is on the alkylene group, rather than at the ester function which is preferably substituted with a $C_1$-$C_6$ alkyl or aryl group), preferably, $C_1$-$C_6$ alkyl or aryl, halogen (preferably, F or Cl), nitro or amine (including a five- or six-membered cyclic alkylene amine, further including a $C_1$-$C_6$ alkyl amine or $C_1$-$C_6$ dialkyl amine which alkyl groups may be substituted with one or two hydroxyl groups), amido, which is preferably substituted with one or two $C_1$-$C_6$ alkyl groups (including a carboxamide which is substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Preferably, the term "substituted"

shall mean within its context of use alkyl, alkoxy, halogen, ester, keto, nitro, cyano and amine (especially including mono- or di-$C_1$-$C_6$ alkyl substituted amines which may be optionally substituted with one or two hydroxyl groups). Any substitutable position in a compound according to the present invention may be substituted in the present invention, but no more than 3, more preferably no more than 2 substituents (in some instances only 1 or no substituents) is present on a ring. Preferably, the term "unsubstituted" shall mean substituted with one or more H atoms.

"Halogen" or "halo" may be fluoro, chloro, bromo or iodo.

A "hydrolyzable moiety" can be methyl, t-butyl, benzyl, p-methoxybenzyl, p-nitrobenzyl, allyl, trityl, methoxymethyl, 2-methoxypropyl, methoxyethoxymethyl, ethoxyethyl, tetrahydropyranyl, tetrahydrothiopyranyl, and trialkylsilyl ethers such as trimethylsilyl ether, triethylsilyl ether, dimethylarylsilyl ether, triisopropylsilyl ether and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates including but not limited to alkyl carbonates having from one to six carbon atoms such as methyl, ethyl, n-propyl, isopropyl, n-butyl, t-butyl; isobutyl, and n-pentyl; alkyl carbonates having from one to six carbon atoms and substituted with one or more halogen atoms such as 2,2,2-trichloroethoxymethyl and 2,2,2-trichloro-ethyl; alkenyl carbonates having from two to six carbon atoms such as vinyl and allyl; cycloalkyl carbonates having from three to six carbon atoms such as cyclopropyl, cyclobutyl, cyclopentyl and cyclohexyl; and phenyl or benzyl carbonates optionally substituted on the ring with one or more $C_{1-6}$ alkoxy, or nitro.

Plumbagin (5-hydroxy-2-methyl-1,4-naphthoquinone), a plant derived naphthoquinone, generally extracted from the roots of *Plumbago* species of three major phylogenetic families viz. Plumbaginaceae, Droseraceae, and Ebenceae, exhibits highly potent biological activities. The compound is well known for its general anti-cancer activity. See, for example, Kuo P L, et al. Mol Cancer Ther 2006, 5:3209-3221; Aziz M H, et al. Cancer Res 2008, 68:9024-9032; Shih Y W, et al. Hepatol Res 2009, 39:998-1009; Srinivas P, et al. Mol Carcinog 2004, 40:201-211; Powolny A A and Singh S V Pharm Res 2008, 25:2171-2180, each of which is incorporated by reference in its entirety. Since its first reported apoptotic activities, the compound has been envisaged as a "lead" molecule for the development of new therapeutic agents for cancer. Efforts have focused on the design and synthesis of novel analogues and derivatives of plumbagin which can exhibit better activity, reduced toxicity, or improved pharmokinetics.

The derivatives of plumbagin described here have been evaluated for apoptotic properties and have been shown to have unexpected selectivity compared to plumbagin itself. Examples of derivatives of plumbagin that have been synthesized include those prepared by Mathew et al. by following the general esterification methods, which were previously studied for their anti-tuberculosis activity. See, for example, Mathew R, et al. Chem Biol Drug Des 2010, 76:34-42, which is incorporated by reference in its entirety.

Derivatives of plumbagin can be tested for anti-cancer potential. Apoptotic potential of the derivatives and plumbagin are evaluated in five human cancer cell lines, such as HepG2 (liver carcinoma), HeLa (cervical carcinoma), MCF-7 (ER-positive) (breast carcinoma), BT-20 (ER-negative) (breast carcinoma) or DU145 (prostrate carcinoma), along with BJ (normal skin fibroblasts) in vitro using MTT and APOPercentage assays. Certain plumbagin derivatives showed significant selective cytotoxicity against cancer cell lines although normal cells (BJ) are unaffected even at higher concentration.

The derivatives of plumbagin can be cytotoxic to human breast cancer cells. By comparison to normal human cells, the compounds can be 2, 3, 4, 5, 8, 10, 15, 20 or more times less cytotoxic to normal human cells compared to human breast cancer cells. In certain embodiments, the $IC_{50}$ value of the disclosed compounds can be less than 20 micromolar, less than 15 micromolar, less than 10 micromolar, or less than 8 micromolar.

A derivative of plumbagin, or a pharmaceutically acceptable salt thereof, can be represented by formula (I) or formula (II):

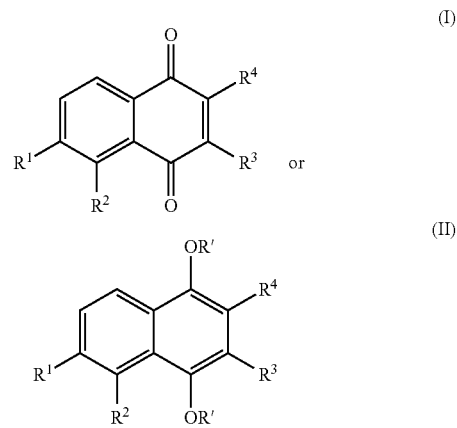

$R^1$ can be H, substituted or unsubstituted $C_1$-$C_{12}$alkyl, cyano, halo, carboxyl, or nitro.

$R^2$ can be H, substituted or unsubstituted $C_1$-$C_{12}$alkyl, or O—R'.

$R^3$ can be H, substituted or unsubstituted $C_1$-$C_{12}$alkyl, —N(R')$_2$, or —O—R'.

$R^4$ can be H, —O—R', or $C_1$-$C_6$ alkyl.

Each R', when present, independently, can be H, substituted or unsubstituted $C_1$-$C_6$alkyl, or a hydrolyzable moiety, such as acyl or trialkylsilyloxy.

In certain embodiments of the compound of formula (I), the double bond between $R^3$ and $R^4$ can be replaced with a single oxygen (to form an epoxy group) or H and CN, respectively.

In certain embodiments, $R^1$ is H.

In certain embodiments, $R^2$ is $R^a$—C(O)—O—, in which $R^a$ is methyl, ethyl, propyl, propenyl, isopropyl, butyl, isobutyl, sec-butyl, pentyl, hexyl, or phenyl.

In certain embodiments, $R^3$ is H.

In certain embodiments, $R^4$ can be H, —O—R' or $C_1$-$C_6$ alkyl.

In certain embodiments, $R^1$ is H and $R^3$ is H.

In certain embodiments, $R^2$ is $R^a$—C(O)—O—, in which $R^a$ is methyl, ethyl, propyl, propenyl, isopropyl, butyl, aryl or heteroaryl, for example, phenyl.

In certain embodiments, $R^4$ is H, OH, or methyl.

Each group $R^1$-$R^5$, for each occurrence, can be, independently, optionally substituted with halo, carboxylic acid, cyano, or nitro.

In other embodiments, the compound, or a pharmaceutically acceptable salt thereof, can be represented by one of the following formulae:

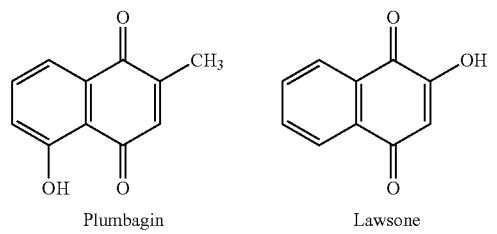

Plumbagin  Lawsone

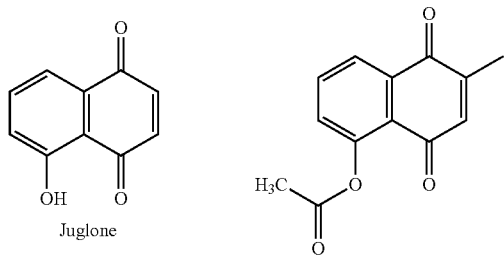

Juglone  Acetyl Plumbagin

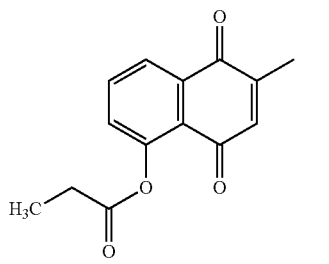

Propionate Plumbagin

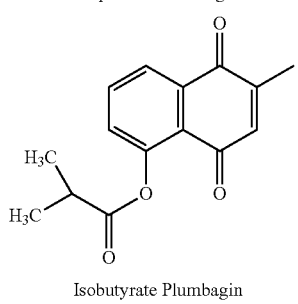

Isobutyrate Plumbagin

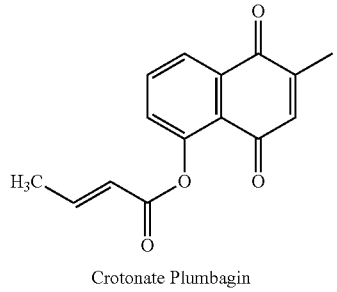

Crotonate Plumbagin

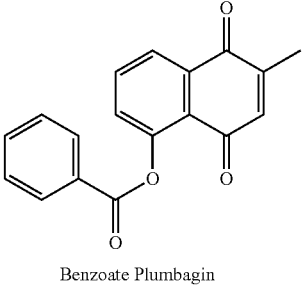

Benzoate Plumbagin

-continued

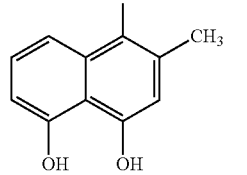

Hydroquinonoid derivative of plumbagin

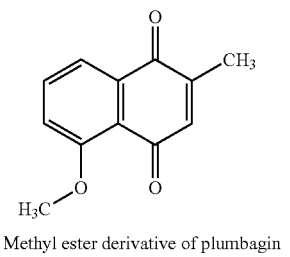

Methyl ester derivative of plumbagin

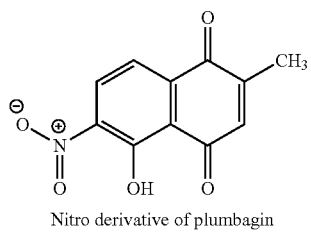

Nitro derivative of plumbagin

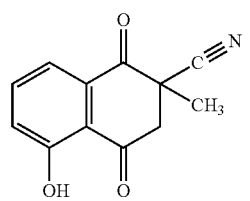

Cyano derivative of plumbagin

The hydroquinonoid, nitro, cyano, and methyl ester derivatives of plumbagin have been studied for their anti-tumor and anti-leishmanial activities. See, for example, Phytother Res 2002; 16:133-137, which is incorporated by reference in its entirety. These hydroquinonoid, nitro, cyano, and methyl ester derivatives of compounds can have unexpected benefits in treating certain cancers.

In another example, an amino acid moiety derivatives of plumbagin (formula (III)) have been synthesized and subsequently screened for antifeedant activity in tobacco caterpillar (*Spodoptera litura*) and castor semi-looper (*Achaea janata*). See, for example, J Agric Food Chem 2009; 57:6090-6094, which is incorporated by reference in its entirety. These amino acid moiety derivatives of plumbagin can have unexpected benefits in treating certain cancers.

(III)

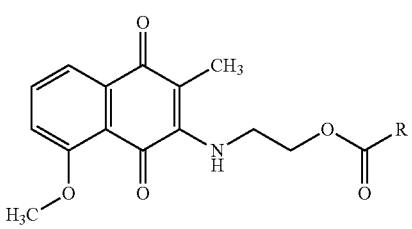

-continued

R = —CH₂—NH—Ac
—CH₂CH—NH—Ac
—SH

In another example, a derivative compound can be a naphthoquinone derivatives of plumbagin, which were mostly substituted at C-3 position through carbon-carbon bond formation, synthesized and screened for their ichthyotoxicity. See, for example, Chem Pharm Bull 1997; 45:437-445, which is incorporated by reference in its entirety. These naphthoquinone derivatives of plumbagin can have unexpected benefits in treating certain cancers. See, for example, formula (IV), formula (V) or formula (VI).

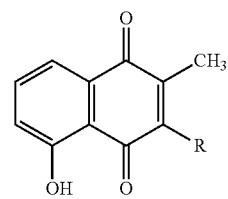
(IV)

R = —CH₂—CO—C₂H₅
—CH₂—CO—C₃H₇
—CH₃—, —C₃H₇, —C₆H₁₃
—CH₂-phenyl, —OH, —OCH₃
—CH—(NHAc)—CH₃
—Br

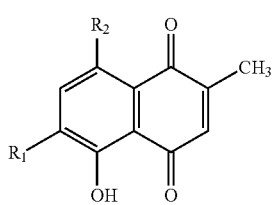
(V)

R1 = —H, —OH
R2 = —H, —OH

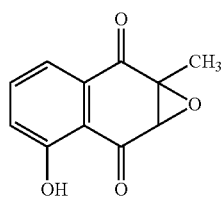
(VI)

In some embodiments, the derivative of plumbagin can be a plumbagin homologue (2-alkyl-1,4-naphthoquinones), including a 3-methyl derivative, which has also been synthesized to evaluate their prostaglandin synthetase (PGS)-inhibition activity. See, for example, Arzneimittelforschung 1984; 34:652-658, which is incorporated by reference in its entirety. These plumbagin homologues can have unexpected benefits in treating certain cancers. See, for example, formula (VII), formula (VIII), formula (IX), formula (X), or formula (XI).

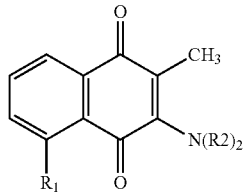
(VII)

R1 = —H, —OH
R2 = —(CH₂)₃—NH—(CH₂)₃—NH₂
—(CH₂)₃—NH—(CH₂)₄—NH(CH₂)₃—NH₂
—(CH₂)—NH₂

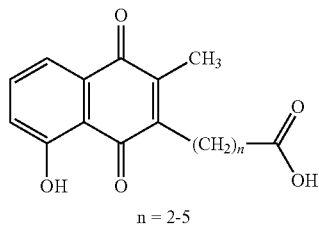
(VIII)

n = 2-5

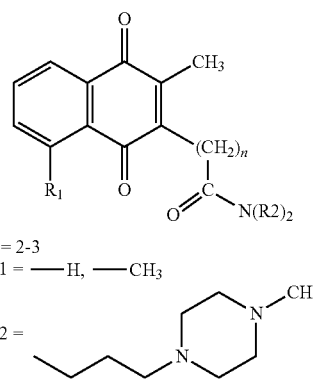
(IX)

n = 2-3
R1 = —H, —CH₃

R2 = 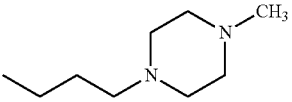

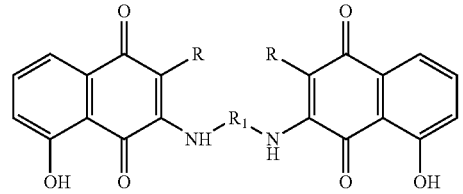
(X)

R = —CH₃
R1 = —(CH₂)₃—NH—(CH₂)₃—CH₃
—(CH₂)₄—CH₃
—(CH₂)₃—NH—(CH₂)₄—NH—(CH₂)₃—CH₃

-continued

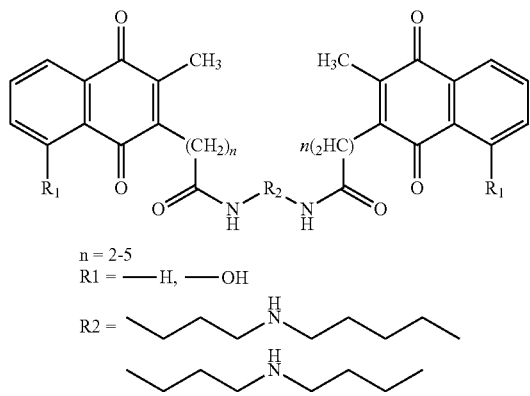

(XI)

n = 2-5
R1 = —H, —OH
R2 = [structure]

A salt of any of the compounds can be prepared. For example, a pharmaceutically acceptable salt can be formed when an amino-containing compound of this invention reacts with an inorganic or organic acid. Some examples of such an acid include hydrochloric acid, hydrobromic acid, hydroiodic acid, sulfuric acid, phosphoric acid, p-bromophenylsulfonic acid, carbonic acid, succinic acid, citric acid, benzoic acid, and acetic acid. Examples of pharmaceutically acceptable salts thus formed include sulfate, pyrosulfate bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, tosylate, methanesulfonate, acetate, citrate, malonate, tartarate, succinate, benzoate, ascorbate, α-ketoglutarate, α-glycerophosphate, sulfate, nitrate, bicarbonate, or carbonate salts. A compound described herein may also form a pharmaceutically acceptable salt when a compound having an acid moiety reacts with an inorganic or organic base. Such salts include those derived from inorganic or organic bases, e.g., alkali metal salts such as sodium, potassium, or lithium salts; alkaline earth metal salts such as calcium or magnesium salts; or ammonium salts or salts of organic bases such as morpholine, piperidine, pyridine, dimethylamine, or diethylamine salts.

It should be recognized that a suitable compound can contain chiral carbon atoms. In other words, it may have optical isomers (enantiomers) or diastereoisomers.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Cancers generally show partial or complete lack of structural organization and functional coordination with the normal tissue and most invade surrounding tissues, metastasize to several sites, and are likely to recur after attempted removal and to cause the death of the patient unless adequately treated. As used herein, the term cancer is used to describe all cancerous disease states applicable to treatment according to the present invention and embraces or encompasses the pathological process associated with all virtually all epithelial cancers, including carcinomas, malignant hematogenous, ascitic and solid tumors. Examples of cancers which may be treated using methods according to the present invention include, without limitation, carcinomas (e.g., squamous-cell carcinomas, adenocarcinomas, hepatocellular carcinomas, and renal cell carcinomas), particularly those of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas. See, for example, The Merck Manual of Diagnosis and Therapy, 17.sup.th ed. (Whitehouse Station, N.J.: Merck Research Laboratories, 1999) 973-74, 976, 986, 988, 991).

In addition to the treatment of ectopic cancers as described above, the present invention also may be used preferably to treat eutopic cancers such as choriocarcinoma, testicular choriocarcinoma, non-seminomatous germ cell testicular cancer, placental cancer (trophoblastic tumor) and embryonal cancer, among others.

The term "additional anticancer agent" includes chemotherapeutic agents selected from the group consisting of microtubule-stabilizing agents, microtubule-disruptor agents, alkylating agents, antimetabolites, epidophyllotoxins, antineoplastic enzymes, topoisomerase inhibitors, inhibitors of cell cycle progression, and platinum coordination complexes. These may be selected from the group consisting of everolimus, trabectedin, abraxane, TLK 286, AV-299, DN-101 pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitors, an AKT inhibitor, a JAK/STAT inhibitor, a checkpoint-1 or 2 inhibitor, a focal adhesion kinase inhibitor, a Map kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR$_1$ KRX-0402, lucanthone, LY 317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258,); 3-[5-(methylsulfonylpiperadinemethyl)-indolylj-quinolone, vatalanib, AG-013736, AVE-0005, the acetate salt of [D-Ser(But) 6, Azgly 10] (pyro-Glu-His-Trp-Ser-Tyr-D-Ser(But)-Leu-Arg-Pro-Azgly-$NH_2$ acetate [$C_{59}H_{84}N_{18}Oi_4$-$(C_2H_4O_2)_x$ where x=1 to 2.4], goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, amsacrine, anagrelide, L-asparaginase, *Bacillus* Calmette-Guerin (BCG) vaccine, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001 ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonists, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa and darbepoetin alfa, among others.

Formulations containing the compounds according to the present invention may take the form of liquid, solid, semi-solid or lyophilized powder forms, such as, for example, solutions, suspensions, emulsions, sustained-release formulations, tablets, capsules, powders, suppositories, creams, ointments, lotions, aerosols, patches or the like, preferably in unit dosage forms suitable for simple administration of precise dosages.

Pharmaceutical compositions according to the present invention typically include a conventional pharmaceutical carrier or excipient and may additionally include other medicinal agents, carriers, adjuvants, additives and the like. The weight percentage ratio of the one or more active ingredients to the one or more excipients can be between about 20:1 to about 1:60, or between about 15:1 to about 1:45, or between about 10:1 to about 1:40, or between about 9:1, 8:1, 7:1, 6:1, 5:1, 4:1, 3:1, 2:1 or 1:1 to about 1:2, 1:3, 1:4, 1:5, 1:6, 1:7, 1:8, 1:9, 1:10, 1:15, 1:20, 1:25, 1:30, or 1:35, and preferably is about 20:1, 19:1, 18:1, 17:1, 16:1, 15:1, 14:1, 13:1, 12:1, 11:1, 10:1, 9:1, 8:1, 7:1, 6:1 or 5:1. In some embodiments, formulations of the invention comprise between about 250 mg to about 500 mg, or between about 300 mg to about 450 mg, or about 325 mg to about 425 mg of total active ingredients and may optionally contain one or more suitable pharmaceutical excipients.

An injectable composition for parenteral administration (e.g. intravenous, intramuscular or intrathecal) will typically contain the compound in a suitable i.v. solution, such as sterile physiological salt solution. The composition may also be formulated as a suspension in an aqueous emulsion.

Liquid compositions can be prepared by dissolving or dispersing the pharmaceutical composition comprising e.g., a CTEP inhibitor, and optional pharmaceutical adjuvants, in a carrier, such as, for example, aqueous saline, aqueous dextrose, glycerol, or ethanol, to form a solution or suspension. For use in an oral liquid preparation, the composition may be prepared as a solution, suspension, emulsion, or syrup, being supplied either in liquid form or a dried form suitable for hydration in water or normal saline.

For oral administration, such excipients include pharmaceutical grades of mannitol, lactose, starch, magnesium stearate, sodium saccharine, talcum, cellulose, glucose, gelatin, sucrose, magnesium carbonate, and the like. If desired, the composition may also contain minor amounts of non-toxic auxiliary substances such as wetting agents, emulsifying agents, or buffers.

When the composition is employed in the form of solid preparations for oral administration, the preparations may be tablets, granules, powders, capsules or the like. In a tablet formulation, the composition is typically formulated with additives, e.g. an excipient such as a saccharide or cellulose preparation, a binder such as starch paste or methyl cellulose, a filler, a disintegrator, and other additives typically used in the manufacture of medical preparations.

Methods for preparing such dosage forms are known or are apparent to those skilled in the art; for example, see Remington's Pharmaceutical Sciences (17th Ed., Mack Pub. Co. 1985). The composition to be administered will contain a quantity of the selected compound in a pharmaceutically effective amount for therapeutic use in a biological system, including a patient or subject according to the present invention.

Methods of treating patients or subjects in need for a particular disease state or infection comprise administration of an effective amount of a pharmaceutical composition comprising therapeutic amounts of one or more of the novel compounds described herein and optionally at least one additional bioactive (e.g. anti-cancer) agent according to the present invention. The amount of active ingredient(s) (including e.g., a CTEP inhibitor) used in the methods of treatment of the instant invention that may be combined with the carrier materials to produce a single dosage form will vary depending upon the host treated, the particular mode of administration. For example, the compositions could be formulated so that a therapeutically effective dosage of between about 0.01, 0.1, 1, 5, 10, 15, 20, 25, 30, 35, 40, 45, 50, 55, 60, 65, 70, 75, 80, 85, 90 or 100 mg/kg of patient/day or in some embodiments, greater than 100, 110, 120, 130, 140, 150, 160, 170, 180, 190 or 200 mg/kg of the novel compounds can be administered to a patient receiving these compositions.

Preferably, pharmaceutical compositions in dosage form according to the present invention comprise a therapeutically effective amount of at least 25 mg of e.g., a CTEP inhibitor, at least 50 mg of e.g., a CTEP inhibitor, at least 60 mg of e.g., a CTEP inhibitor, at least 75 mg of e.g., a CTEP inhibitor, at least 100 mg of e.g., a CTEP inhibitor, at least 150 mg of e.g., a CTEP inhibitor, at least 200 mg of e.g., a CTEP inhibitor, at least 250 mg of e.g., a CTEP inhibitor, at least 300 mg of e.g., a CTEP inhibitor, about 350 mg of e.g., a CTEP inhibitor, about 400 mg of e.g., a CTEP inhibitor, about 500 mg of e.g., a CTEP inhibitor, about 750 mg of e.g., a CTEP inhibitor, about 1 g (1,000 mg) of e.g., a CTEP inhibitor, alone or in combination with a therapeutically effective amount of at least one additional anti-cancer agent.

Preferred embodiments of the pharmaceutical compositions of the invention comprise between about 250 mg to about 500 mg, or between about 300 mg to about 450 mg, or about 325 mg to about 425 mg, most preferably about 380 mg of e.g., a CTEP inhibitor.

The dose of a derivative of plumbagin administered to a subject can be less than 10 µg, less than 25 µg, less than 50 µg, less than 75 µg, less than 0.10 mg, less than 0.25 mg, less than 0.5 mg, less than 1 mg, less than 2.5 mg, less than 5 mg, less than 10 mg, less than 15 mg, less than 20 mg, less than 50 mg, less than 75 mg, less than 100 mg, or less than 500 mg.

The activities of a compound described herein can be evaluated by methods known in the art, e.g., MTT (3-[4,5-dimethylthiazol-2-yl]-2,5-diphenyltetrazolium bromide) assay, APOPercentage, clonogenic assay, ATP assay, or Extreme Drug Resistance (EDR) assay. See Freuhauf, J. P. and Manetta, A., Chemosensitivity Testing in Gynecologic Malignancies and Breast Cancer 19, 39-52 (1994), which is incorporated by reference in its entirety. The results are then plotted to generate drug response curves, which allow $IC_{50}$ values (the concentration of a compound required to inhibit 50% of the population of the treated cells) to be determined. The amount of the compound, or an active salt or derivative thereof, required for use in treatment can vary not only with the particular salt selected but also with the route of administration, the nature of the condition being treated and the age and condition of the patient and can be ultimately at the discretion of the attendant physician or clinician. In general, however, a dose can be in the range of from about 0.01 to about 10 mg/kg of body weight per day.

Other anti-cancer assays are well-known in the art, including in vitro exposure of agents to tumor cells and in vivo antitumor assays in rodent models and rarely, in larger animals.

Purely by way of example, comparing measured cancer cell sample viability, MOMP levels and/or levels of apoptosis-associated proteins with cell viability, MOMP levels and/or levels of apoptosis-associated proteins in a control cancer cell sample and comparing measured cancer cell CETP levels with CTEP levels of a control cancer cell sample can include comparative level differences of about between about 5-10%, or about 10-15%, or about 15-20%, or about 20-25%, or about 25-30%, or about 30-35%, or about 35-40%, or about 40-45%, or about 45-50%, or about 50-55%, or about 55-60%, or about 60-65%, or about 65-70%, or about 70-75%, or about 75-80%, or about 80-85%, or about 85-90%, or about 90-95%, or about 95-100%, or about 100-110%, or about 110-120%, or about 120-130%, or about 130-140%, or about 140-150%, or about 150-160%, or about 160-170%, or about 170-180%, or about 180-190%, or 190-200%, or about 200-210%, or 210-220%, or 220-230%, or about 230-240%, or about 240-250%, or 250-260%, or about 260-270%, or about 270-280%, or about 280-290%, or about 290-300%, or differences of about between about +50% to about ±0.5%, or about ±45% to about ±1%, or about ±40% to about 1.5%, or about ±35% to about ±2.0%, or about ±30% to about ±2.5%, or about ±25% to about ±3.0%, or about ±20% to about ±3.5%, or about ±15% to about +4.0%, or about ±10% to about +5.0%, or about ±9% to about ±1.0%, or about ±8% to about ±2%, or about ±7% to about ±3%, or about ±6% to about +5%, or about ±5%, or about ±4.5%, or about ±4.0%, or about ±3.5%, or about ±3.0%, or about +2.5%, or about ±2.0%, or about +1.5%, or about ±1.0%.

A "biomarker" is any gene or protein whose level of expression in a biological sample is altered compared to that of a pre-determined level. The pre-determined level can be a level found in a biological sample from a normal or healthy subject. Biomarkers include genes and proteins, and variants and fragments thereof. Such biomarkers include DNA comprising the entire or partial sequence of the nucleic acid sequence encoding the biomarker, or the complement of such a sequence. The biomarker nucleic acids also include RNA comprising the entire or partial sequence of any of the nucleic acid sequences of interest. A biomarker protein is a protein encoded by or corresponding to a DNA biomarker of the invention. A biomarker protein comprises the entire or partial amino acid sequence of any of the biomarker proteins or polypeptides. Biomarkers can be detected, e.g. by nucleic acid hybridization, antibody binding, activity assays, polymerase chain reaction (PCR), Si nuclease assay and gene chip.

A "control" as used herein may be a positive or negative control as known in the art and can refer to a control cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. For instance, as can be appreciated by a skilled artisan, a control may comprise data from one or more control subjects that is stored in a reference database. The control may be a subject who is similar to the test subject (for instance, may be of the same gender, same race, same general age and/or same general health) but who is known to not have a fibrotic disease. As can be appreciated by a skilled artisan, the methods of the invention can also be modified to compare a test subject to a control subject who is similar to the test subject (for instance, may be of the same gender, same race, same general age and/or same general health) but who is known to express symptoms of a disease. In this embodiment, a diagnosis of a disease or staging of a disease can be made by determining whether protein or gene expression levels as described herein are statistically similar between the test and control subjects.

The terms "level" and/or "activity" as used herein further refer to gene and protein expression levels or gene or protein activity. For example, gene expression can be defined as the utilization of the information contained in a gene by transcription and translation leading to the production of a gene product.

In certain non-limiting embodiments, an increase or a decrease in a subject or test sample of the level of measured biomarkers (e.g. proteins or gene expression) as compared to a comparable level of measured proteins or gene expression in a control subject or sample can be an increase or decrease in the magnitude of approximately 5,000-10,000%, or approximately ±2,500-5,000%, or approximately +1,000-2,500%, or approximately ±500-1,000%, or approximately +250-500%, or approximately ±100-250%, or approximately 50-100%, or approximately +25-50%, or approximately ±10-25%, or approximately ±10-20%, or approximately ±10-15%, or approximately +5-10%, or approximately ±1-5%, or approximately ±0.5-1%, or approximately +0.1-0.5%, or approximately ±0.01-0.1%, or approximately ±0.001-0.01%, or approximately ±0.0001-0.001%.

The values obtained from controls are reference values representing a known health status and the values obtained from test samples or subjects are reference values representing a known disease status. The term "control", as used herein, can mean a sample of preferably the same source (e.g. blood, serum, tissue etc.) which is obtained from at least one healthy subject to be compared to the sample to be analyzed. In order to receive comparable results the control as well as the sample should be obtained, handled and treated in the same way. In certain examples, the number of healthy individuals used to obtain a control value may be at least one, preferably at least two, more preferably at least five, most preferably at least ten, in particular at least twenty. However, the values may also be obtained from at least one hundred, one thousand or ten thousand individuals.

A level and/or an activity and/or expression of a translation product of a gene and/or of a fragment, or derivative, or variant of said translation product, and/or the level or activity of said translation product, and/or of a fragment, or derivative, or variant thereof, can be detected using an immunoassay, an activity assay, and/or a binding assay. These assays can measure the amount of binding between said protein molecule and an anti-protein antibody by the use of enzymatic, chromodynamic, radioactive, magnetic, or luminescent labels which are attached to either the anti-protein antibody or a secondary antibody which binds the anti-protein antibody. In addition, other high affinity ligands may be used. Immunoassays which can be used include e.g. ELISAs, Western blots and other techniques known to those of ordinary skill in the art (see Harlow and Lane, Antibodies: A Laboratory Manual, Cold Spring Harbor Laboratory Press, Cold Spring Harbor, N.Y., 1999 and Edwards R, Immunodiagnostics: A Practical Approach, Oxford University Press, Oxford; England, 1999). All these detection techniques may also be employed in the format of microarrays, protein-arrays, antibody microarrays, tissue microarrays, electronic biochip or protein-chip based technologies (see Schena M., Microarray Biochip Technology, Eaton Publishing, Natick, Mass., 2000).

Certain diagnostic and screening methods of the present invention utilize an antibody, preferably, a monocolonal antibody, capable of specifically binding to a protein as described herein or active fragments thereof. The method of utilizing an antibody to measure the levels of protein allows for non-invasive diagnosis of the pathological states of kidney diseases. In a preferred embodiment of the present invention, the antibody is human or is humanized. The preferred antibodies may be used, for example, in standard radioimmunoassays or enzyme-linked immunosorbent assays or other assays which utilize antibodies for measurement of levels of protein in sample. In a particular embodiment, the antibodies of the present invention are used to detect and to measure the levels of protein present in a sample.

Humanized antibodies are antibodies, or antibody fragments, that have the same binding specificity as a parent antibody, (i.e., typically of mouse origin) and increased human characteristics. Humanized antibodies may be obtained, for example, by chain shuffling or by using phage display technology. For example, a polypeptide comprising a heavy or light chain variable domain of a non-human antibody specific for a disease related protein is combined with a repertoire of human complementary (light or heavy) chain variable domains. Hybrid pairings specific for the antigen of interest are selected. Human chains from the selected pairings may then be combined with a repertoire of human complementary variable domains (heavy or light) and humanized antibody polypeptide dimers can be selected for binding specificity for an antigen. Techniques described for generation of humanized antibodies that can be used in the method of the present invention are disclosed in, for example, U.S. Pat. Nos. 5,565,332; 5,585,089; 5,694,761; and 5,693,762. Furthermore, techniques described for the production of human antibodies in transgenic mice are described in, for example, U.S. Pat. Nos. 5,545,806 and 5,569,825.

In order to identify small molecules and other agents useful in the present methods for treating a cancer by modulating the activity and expression of a disease-related protein and biologically active fragments thereof can be used for screening therapeutic compounds in any of a variety of screening techniques. Fragments employed in such screening tests may be free in solution, affixed to a solid support, borne on a cell surface, or located intracellularly. The blocking or reduction of biological activity or the formation of binding complexes between the disease-related protein and the agent being tested can be measured by methods available in the art.

Other techniques for drug screening which provide for a high throughput screening of compounds having suitable binding affinity to a protein, or to another target polypeptide useful in modulating, regulating, or inhibiting the expression and/or activity of a disease, are known in the art. For example, microarrays carrying test compounds can be prepared, used, and analyzed using methods available in the art. See, e.g., Shalon, D. et al., 1995, International Publication No. WO95/35505, Baldeschweiler et al., 1995, International Publication No. WO95/251116; Brennan et al., 1995, U.S. Pat. No. 5,474,796; Heller et al., 1997, U.S. Pat. No. 5,605,662.

Identifying small molecules that modulate protein activity can also be conducted by various other screening techniques, which can also serve to identify antibodies and other compounds that interact with proteins identified herein and can be used as drugs and therapeutics in the present methods. See, e.g., Enna et al., eds., 1998, Current Protocols in Pharmacology, John Wiley & Sons, Inc., New York N.Y. Assays will typically provide for detectable signals associated with the binding of the compound to a protein or cellular target. Binding can be detected by, for example, fluorophores, enzyme conjugates, and other detectable labels well known in the art. The results may be qualitative or quantitative.

For screening the compounds for specific binding, various immunoassays may be employed for detecting, for example, human or primate antibodies bound to the cells. Thus, one may use labeled anti-hIg, e.g., anti-hIgM, hIgG or combinations thereof to detect specifically bound human antibody. Various labels can be used such as radioisotopes, enzymes, fluorescers, chemiluminescers, particles, etc. There are numerous commercially available kits providing labeled anti-hIg, which may be employed in accordance with the manufacturer's protocol.

In one embodiment, a kit can comprise: (a) at least one reagent which is selected from the group consisting of (i) reagents that detect a transcription product of the gene coding for a protein marker as described herein (ii) reagents that detect a translation product of the gene coding for proteins, and/or reagents that detect a fragment or derivative or variant of said transcription or translation product; (b) optionally, one or more types of cells, including engineered cells in which cellular assays are to be conducted; (c) instructions for diagnosing, or prognosticating a disease, or determining the propensity or predisposition of a subject to develop such a disease or of monitoring the effect of a treatment by determining a level, or an activity, or both said level and said activity, and/or expression of said transcription product and/or said translation product and/or of fragments, derivatives or variants of the foregoing, in a sample obtained from said subject; and comparing said level and/or said activity and/or expression of said transcription product and/or said translation product and/or fragments, derivatives or variants thereof to a reference value representing a known disease status (patient) and/or to a reference value representing a known health status (control) and/or to a reference value; and analyzing whether said level and/or said activity and/or expression is varied compared to a reference value representing a known health status, and/or is similar or equal to a reference value representing a known disease status or a reference value; and diagnosing or prognosticating a disease, or determining the propensity or predisposition of said subject to develop such a disease, wherein a varied or altered level, expression or activity, or both said level and said activity, of said transcription product and/or said translation product and/or said fragments, derivatives or variants thereof compared to a reference value representing a known health status (control) and/or wherein a level, or activity, or both said level and said activity, of said transcription product and/or said translation product and/or said fragments, derivatives or variants thereof is similar or equal to a reference value and/or to a reference value representing a known disease stage, indicates a diagnosis or prognosis of a disease, or an increased propensity or predisposition of developing such a disease, a high risk of developing signs and symptoms of a disease.

Reagents that selectively detect a transcription product and/or a translation product of the gene coding for proteins can be sequences of various length, fragments of sequences, antibodies, aptamers, siRNA, microRNA, and ribozymes. Such reagents may be used also to detect fragments, derivatives or variants thereof.

In one embodiment, the invention provides a method of treating a subject who suffers from a cancer, the method comprising administering to the subject a therapeutically effective amount of Cholesteryl Ester Transfer Protein (CETP) inhibitor selected from the group consisting of acetyl plumbagin, rosuvastatin, rivastatin, pitavastatin, lovastatin, simvastatin, pravastatin, fluvastatin, dalceptrpib, anacetrapib, evacetrapib, torcetrapib, atorvastatin (preferably atorvastatin hemi-calcium), cerivastatin, CETP inhibitors described in U.S. Pat. Nos. 7,652,049, 6,140,343, 6,197,786, 6,723,752 (preferably (2R)-3-{[3-(4-Chloro-3-ethyl-phenoxy)-phenyl]-[[3-(1,1,2,2-tetrafluoro-ethoxy)-phenyl]-methyl]-amino}-1,1,1-trifluoro-2-propanol), and U.S. Pat. No. 5,512,548, CETP-inhibitory rosenonolactone derivatives and phosphate-containing analogs of cholesteryl ester described in *J. Antibiot.*, 49(8): 815-816 (1996) and *Bioorg. Med. Chem. Lett.;* 6:1951-1954 (1996), propanethioic acid, 2-methyl-, S-[2-[[[1-(2 ethylbutyl)cyclohexyl]carbonyl]amino]phenyl]ester (Dalcetrapib), S-[2-(1-isopentylcyclohexanecarbonylamino)phenyl]2,2-dimethylthiopropionate; S-[2-(1-isopentylcyclohexanecarbonylamino)phenyl]2-acetylamino-3-phenylthiopropionate; S-[2-(1-isopentylcyclohexanecarbonylamino)phenyl]3-pyridinethiocarboxylate; S-[2-(1-isopentylcyclohexanecarbonylamino)phenyl]chlorothioacetate; S-[2-(1-isopentylcyclohexanecarbonylamino)phenyl]methoxythioacetate; S-[2-(1-isopentylcyclohexanecarbonylamino)phenyl]thiopropionate; S-[2-(1-isopentylcyclohexanecarbonylamino)phenyl]phenoxy-thioacetate; S-[2-(1-isopentylcyclohexanecarbonylamino)phenyl]2-methylthiopropionate; S-[2-(1-isopentylcyclohexanecarbonylamino)phenyl]4-chlorophenoxythioacetate; S-[2-(1-isopentylcyclohexanecarbonylamino)phenyl]cyclopropanethiocarboxylate; S-[2-(1-isopentylcyclohexanecarbonylamino)phenyl]2-acetylamino-4-carbamoylthiobutyrate; S-[2-(1-isopentylcyclohexanecarbonylamino)phenyl]2-hydroxy-2-methylthiopropionate; S-[2-(1-isopentylcyclopentanecarbonylamino)phenyl]2,2-dimethylthiopropionate; S-[2-(1-isopentylcyclopentanecarbonylamino)phenyl]thioacetate; S-[4,5-dichloro-2-(1-isopentylcyclohexanecarbonylamino)-phenyl]2,2-dimethylthiopropionate; S[4,5-dichloro-2-(1-isopentylcyclopentanecarbonylamino)-phenyl]2,2-dimethy- lthiopropionate; S-[2-(1-isopentylcyclohexanecarbonylamino)-4-trifluoromethylphenyl]2,2-dimethylthiopropionate; O-methyl S-[2-(1-isopentylcyclohexanecarbonylaminophenyl monothiocarbonate; S-[2-(1-methylcyclohexanecarbonylamino)phenyl]S-phenyldithiocarbonate; S-[2-(1-isopentylcyclohexanecarbonylamino)phenyl]N-phenylthiocarbarnate; S-[2-(pivaloylamino)-4-trifluoromethylphenyl]2,2-dimethylthiopropionate; S-[4,5-dichloro-2-(1-cyclopropylcyclohexanecarbonylamino)phenyl]2,2-dimethylthiopropionate; S-[4,5-dichloro-2-(2-cyclohexylpropionylamino)phenyl]2,2-dimethylthiopropionate; S-[4,5-dichloro-2-(1-pentylcyclohexanecarbonylamino)-phenyl]2,2-dimethylthiopropionate; S-[4,5-dichloro-2-(1-cyclopropylmethyl- cyclohexane- carbonylamino)phenyl]2,2-dimethylthiopropionate; S-[4,5-dichloro-2-(1-cyclohexylmethylcyclohexanecarbonylamino)phenyl]2,2-dimethylthiopropionate; S-[4,5-dichloro-2-(1-isopropylcyclohexanecarbonylamino)-phenyl]2,2-dimethylthiopropionate; S-[4,5-dichloro-2-(1-isopentylcycloheptanecarbonylamino)-phenyl]2,2-dimethylthiopropionate; S-[4,5-dichloro-2-(1-isopentylcyclobutanecarbonylamino)-phenyl]2,2-dimethylthiopropionate; S-[2-(1-isopentylcyclohexanecarbonylamino)-4-nitrophenyl]2,2-dimethylthiopropionate; S-[4-cyano-2-(1-isopentylcyclohexanecarbonylamino)phenyl]2,2-dimethylthiopropionate; S-[4-chloro-2-(1-isopentylcyclohexanecarbonylamino)phenyl]2,2-dimethylthiopropionate; S-[5-chloro-2-(1-isopentylcyclohexanecarbonylamino)phenyl]2,2-dimethylthiopropionate; S-[4-fluoro-2-(1-isopentylcyclohexanecarbonylamino)phenyl]2,2-dimethylthiopropionate; S-[4,5-difluoro-2-(1-isopentylcyclohexanecarbonylamino)-phenyl]2,2-dimethylthiopropionate; S-[5-fluoro-2-(1-isopentylcyclohexanecarbonylamino)phenyl]2,2-dimethylthiopropionate; bis-[4,5-dichloro-2-(1-isopentylcyclohexanecarbonylamino)-phenyl]disulfide; 2-tetrahydrofurylmethyl-2-(1-isopentylcyclohexanecarbonylamino)phenyl disulfide; N-(2-mercaptophenyl)-1-ethylcyclohexanecarboxamide; N-(2-mercaptophenyl)-1-propylcyclohexanecarboxamide; N-(2-mercaptophenyl)-1-butylcyclohexanecarboxamide; N-(2-mercaptophenyl)-1-isobutylcyclohexanecarboxamide; S-[2-(1-isopentylcyclohexanecarbonylamino)phenyl]cyclohexanethiocarboxylate; S-[2-(1-isopentylcyclohexanecarbonylamino)phenyl]thiobenzoate; S-[2-(1-isopentylcyclohexanecarbonylamino)phenyl]5-carboxythiopentanoate; S-[2-(1-isopentylcyclohexanecarbonylamino)-4-methylphenyl]thioacetate; bis-[2-[1-(2-ethylbutyl)cyclohexanecarbonylamino]phenyl] disulfide; N-(2-mercaptophenyl)-1-(2-ethylbutyl)cyclohexanecarboxamide; S[2-[1-(2-ethylbutyl)cyclohexanecarbonylamino]phenyl]2-methylthiopropionate; S-[2-(1-isobutylcyclohexanecarbonylamino)phenyl]2-methylthiopropionate-; S-[2-[1-(2-ethylbutyl)cyclohexanecarbonylamino]phenyl]-acetylpiperidine-4-thiocarboxylate; S-[2-[1-(2-ethylbutyl)cyclohexanecarbonylamino]phenyl]thioacetate; S-[2-[1 (2-ethylbutyl)cyclohexanecarbonylamino]phenyl]2,2-dimethylthiopropionate; S-[2-[1-(2-ethylbutyl)cyclohexanecarbonylamino]phenyl]methoxythio-acetate; S-[2-[1-(2-ethylbutyl)cyclohexanecarbonylamino]phenyl]2-hydroxy-2-methylthiopropionate; S-[2-[1-(2-ethylbutyl)cyclohexanecarbonylamino]phenyl]4-chlorophenoxythioacetate; S-[2-(1-isobutylcyclohexanecarbonylamino)phenyl]4-chlorophenoxythioacetate; and S-[2-(1-isobutylcyclohexanecarbonylarnino)phenyl]-1-acetyl-piperidine-4-thiocarboxylate and analogs, derivatives, pharmaceutically acceptable salts, enantiomers, diastereomers, solvates and polymorphs thereof.

Preferred Cholesteryl Ester Transfer Protein (CETP) inhibitors include compounds selected from the group consisting of rosuvastatin, rivastatin, pitavastatin, lovastatin, simvastatin, pravastatin, fluvastatin, dalceptrpib, anacetrapib, evacetrapib, torcetrapib, atorvastatin (preferably atorvastatin hemi-calcium), cerivastatin and analogs, derivatives, pharmaceutically acceptable salts, enantiomers, diastereomers, solvates and polymorphs thereof.

In certain embodiments, a subject suffering from a cancer is administered or co-administered one or more anticancer agents selected from the group consisting of tamoxifen, paclitaxel, fluorouracil (5-FU), plumbagin (5-hydroxy-2-methyl-1,4-naphthoquinone), or an analog, derivative, pharmaceutically acceptable salt, enantiomer, diastereomer, solvate or polymorph thereof. The subject may suffer from a form of refractory breast cancer, may have developed an acquired anti-estrogen resistance and/or may exhibit an intrinsic resistance to anti-estrogen and anti-HER2 therapies.

In certain embodiments, a subject is co-administered a therapeutically effective amount of:
(a) acetyl plumbagin;
(b) one or more additional anticancer agents selected from the group consisting of tamoxifen, paclitaxel and fluorouracil (5-FU); and
(c) optionally, a Cholesteryl Ester Transfer Protein (CETP) inhibitor selected from the group consisting of rosuvastatin, rivastatin, pitavastatin, lovastatin, simvastatin, pravastatin, fluvastatin, dalceptrpib, anacetrapib, evacetrapib, torcetrapib, atorvastatin (preferably atorvastatin hemi-calcium), cerivastatin and analogs, derivatives, pharmaceutically acceptable salts, enantiomers, diastereomers, solvates and polymorphs thereof.

Other embodiments provide a method of improving the clinical outcome of a subject who suffers from a cancer and who is undergoing treatment with one or more anticancer agents selected from the group consisting of tamoxifen, paclitaxel and fluorouracil (5-FU), the method comprising co-administering to the subject one or more compounds selected from the group consisting of plumbagin (5-hydroxy-2-methyl-1,4-naphthoquinone), a compound of formula (I) or formula (II), and the analogs, derivatives, pharmaceutically acceptable salts, enantiomers, diastereomers, solvates and polymorphs thereof:

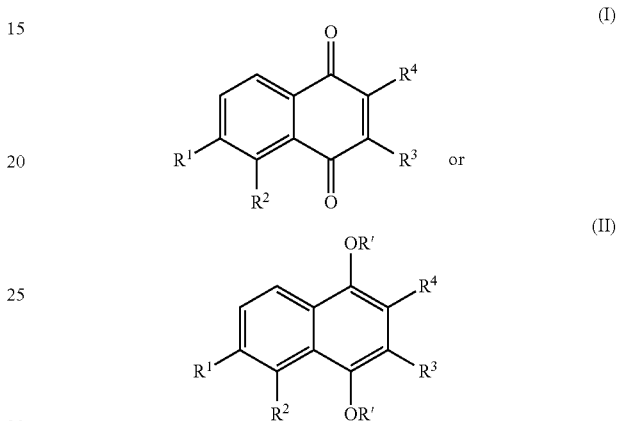

wherein R' is H, substituted or unsubstituted $C_1$-$C_{12}$alkyl, cyano, halo, carboxyl, or nitro;

$R^2$ is H, substituted or unsubstituted $C_1$-$C_{12}$alkyl, or O—R';

$R^3$ is H, substituted or unsubstituted $C_1$-$C_{12}$alkyl, —N(R')$_2$, or —O—R';

$R^4$ is H, —O—R', or $C_1$-$C_6$ alkyl; and each R', when present, independently, is H, substituted or unsubstituted $C_1$-$C_6$alkyl, or a hydrolyzable moiety, such as acyl or trialkylsilyloxy.

In still other embodiments, a subject who suffers from a cancer is administered a therapeutically effective amount of one or more compositions selected from the group consisting of a Cholesteryl Ester Transfer Protein (CETP) inhibiting antisense oligonucleotide, a Cholesteryl Ester Transfer Protein (CETP) inhibiting siRNA and an anti-Cholesteryl Ester Transfer Protein (CETP) antibody.

One illustrative Cholesteryl Ester Transfer Protein (CETP) inhibiting antisense oligonucleotide which can be used in methods and compositions of the invention has the sequence (5'-CAGCACTTTAATGCCAGTGG-3'), wherein the sequence contains 2'-O-methoxyethyl (2' MOE) groups at positions 1-5 and 15-20 which are targeted to human CETP. See Bell, et al., October 2013, *The Journal of Lipid Research*, 54, 2647-2657. Other illustrative Cholesteryl Ester Transfer Protein (CETP) inhibiting antisense oligonucleotide have one of the sequences identified as SEQ ID NOS. 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50 of PCT WO2003014306, wherein such sequences optionally comprises at least one modified internucleoside linkage (e.g. a phosphorothioate linkage) and/or at least one modified sugar moiety (e.g. a 2'-O-methoxyethyl sugar moiety), and/or at least one modified nucleobase (e.g. a 5-methylcytosine). In some embodiments, the oligonucleotide has at least about 70%, 75%, 80%, 85%, 90% or 95% complementarity with a nucleic acid encoding human Cholesteryl Ester Transfer Protein (CETP). In other illustrative embodiments, the oligonucleotide specifically hybridizes with a nucleotide sequence encoding human Cholesteryl Ester Transfer Protein (CETP), wherein the nucleotide sequence comprises a translation initiation codon, a termination codon, a coding region, a 5' untranslated region, a 3' untranslated region, an intron:exon junction or an exon:intron junction.

In other embodiments, a subject suffering from a cancer is administered a Cholesteryl Ester Transfer Protein (CETP) inhibiting double stranded short interfering RNA (ds siRNA), wherein one strand of the double-stranded siRNA molecule comprises a nucleotide sequence that is complementary to a nucleotide sequence of a CETP gene or a portion thereof, and wherein a second strand of the double-stranded siRNA molecule comprises a nucleotide sequence that is complementary to a nucleotide sequence of a CETP gene RNA or a portion thereof. An illustrative Cholesteryl Ester Transfer Protein (CETP) inhibiting double stranded short interfering RNA (ds siRNA) can have at least about 70%, 75%, 80%, 85%, 90% or 95% complementarity with a CTEP inhibiting ds siRNA described in United States Patent Application Document No. 20050171040, the complete disclosure of which is hereby incorporated by reference.

In still other embodiments, a subject who suffers from a cancer is administered a Cholesteryl Ester Transfer Protein (CETP) inhibiting antibody or a fragment thereof.

Preferred Cholesteryl Ester Transfer Protein (CETP) inhibiting antibodies include a humanized monoclonal antibody or a F(ab')$_2$ or Fab' fragment thereof, and the CTEP inhibiting antibodies and antibody fragments described or referenced in United States Patent Application Document No. 20140328851, the complete disclosure of which is hereby incorporated by reference.

The invention is illustrated further in the following non-limiting examples.

Example 1

PL and AP Induce Intrinsic Apoptosis in MCF-7 Cells

We have previously shown that Acetyl Plumbagin (AP) has selective activity against MCF-7 (ER positive breast cancer (BC) cells) as compared to normal skin fibroblasts (BJ) and triple negative BT20 BC cells [1]. We further sought to characterize the timeline of molecular events and specific pathway of apoptosis induced by AP in comparison to its parent molecule PL in MCF-7 cells. As a first step, MCF-7 cells were treated with 1, 2.5, 5 and 10 μM PL or AP for 24 h and percentage viability was determined after 24 h using the MTT assay. Both 1 and 2.5 μM concentrations of PL and AP had no significant effect on cell viability however 5 and 10 μM reduced cell viability by 80% or greater (FIG. 1A). Next the effect of 10 μM PL drug on cell viability over time was determined. PL and AP reduced cell viability to 50% in as early as 6 h (FIG. 1B). The percentage of cells undergoing apoptosis at the early time points i.e. 2 and 6 h was determined by the APOPercentage assay. APOPercentage dye binds to extracellularly exposed phosphatidylserine (PS) on the plasma membrane of apoptotic cells. After induction with PL and AP, an approximately similar level of apoptosis i.e. 20% and 45% was observed at 2 and 6 h respectively (FIG. 1C).

Figure 2:
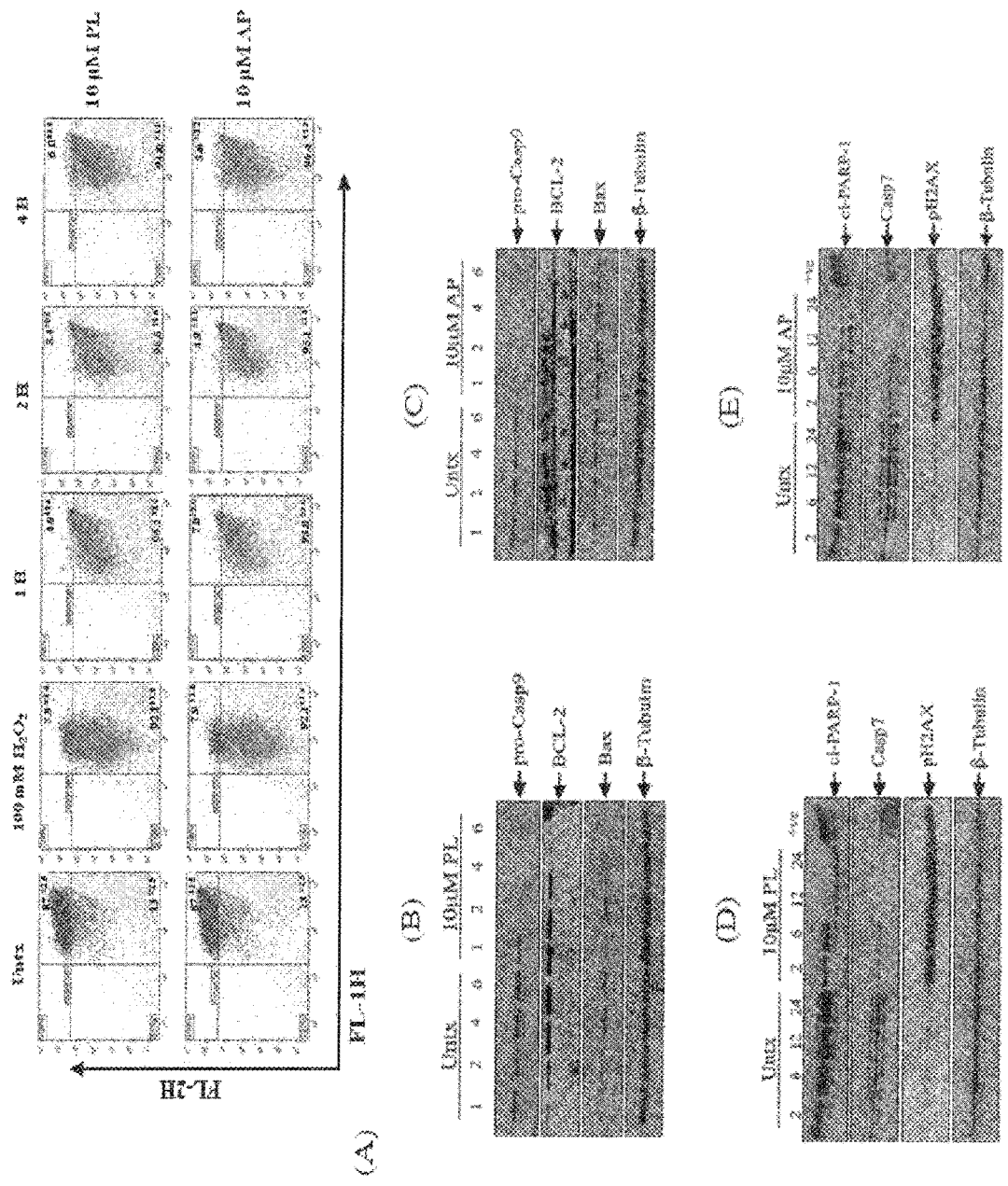
FIG. 2: Mode of induction in MCF-7 cells after treatment with AP and PL was determined by measuring changes in MOMP and levels of apoptosis-associated proteins. The cells were incubated with 10 µM AP and PL for different time intervals to capture the timeline of apoptosis induction in MCF-7 cells. The changes in MOMP were measured using flow cytometry after treating MCF-7 cells with PL and AP for 1, 2 and 4 h (A). The alteration in expression of several apoptosis-associated proteins were determined using western blotting after incubating MCF-7 cells for 1, 2, 4, 6 h with PL (C, E) and AP (D. F).

Since 50% of cells were observed to undergo apoptosis within 6 h of treatment, further studies were performed within this timeframe to establish the chronology of apoptotic events. The changes in Mitochondrial Outer Membrane Potential (MOMP) and proteins involved in the apoptotic cascade were assessed (FIG. 2). Untreated cells yielded higher fluorescence in the FL-2 channel while lower fluorescent values, typical of disrupted MOMP, were observed in cells (FIG. 2A). treated with 10 μM PL, AP and 100 mM $H_2O_2$ (as a positive control).

Intrinsic apoptosis is activated by the mitochondria where MOMP is reduced and the imbalance between pro- and anti-apoptotic factors results in activation of caspases 9, 3 and 7, cleavage of caspase substrate like PARP-1 (Poly [ADP-ribose] polymerase 1) and fragmentation of DNA. After treatment with 10 μM PL and AP alterations in the ratio of Bax and Bcl2 were observed and pro-caspase 9 levels were reduced (FIGS. 2B and C). A reduction of pro-caspase 7 was observed as early as 2 and 6 h in cells treated with PL while pro-caspase 7 was reduced at 12 h in cells treated with AP (FIGS. 2D and E). cl-PARP-1 a substrate of caspase 3/7 was substantially reduced from full length to the cleaved fragment at the 12 and 24 h time points. The expression of the DNA damage marker pH2AX was significantly increased as early as 2 h in both PL and AP treated MCF-7 cells and remained elevated for the duration of the experiment. The data suggests that both PL and AP activate the intrinsic apoptosis pathway in MCF-7 cells.

Example 2

In Vivo Efficacy and Toxicity Profiles in Mouse MCF-7 Xenograft Model of BC

Figure 3:
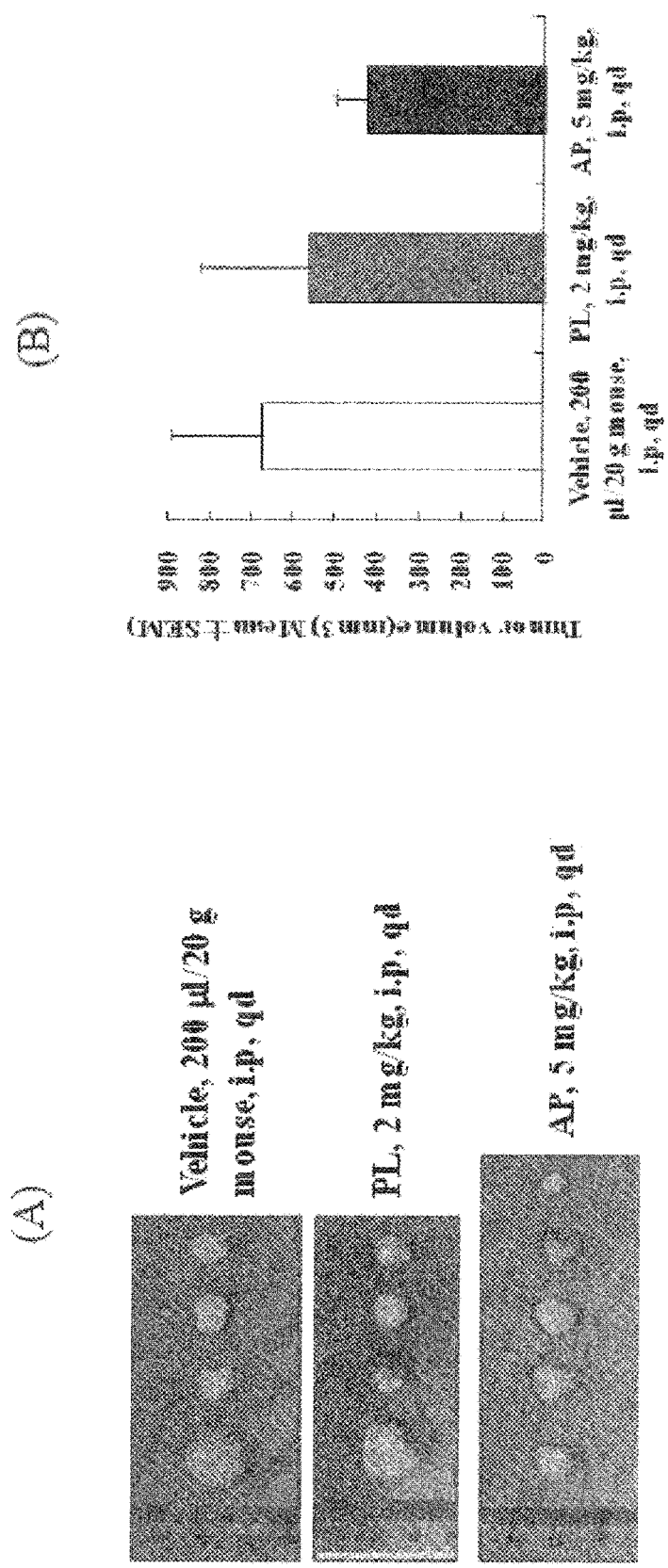
FIG. 3: Comparative efficacy and toxicity study in MCF-7 xenograft nude mouse model of BC. The efficacy of single i.p. injection of vehicle, PL (2 mg/kg) and AP (5 mg/kg) in 5 mice in each group was compared over a period of 21 days. The comparison of tumor sizes (A), tumor volume (B) and body weight (C) demonstrated the efficacy of compound AP as compared to PL. Plasma levels of parameters ALT (D) and AST (E) representing liver toxicity were estimated in vehicle, PL and AP treated mice groups showing that AP even reduced vehicle associated toxicity in treated mice.
Figure 3:
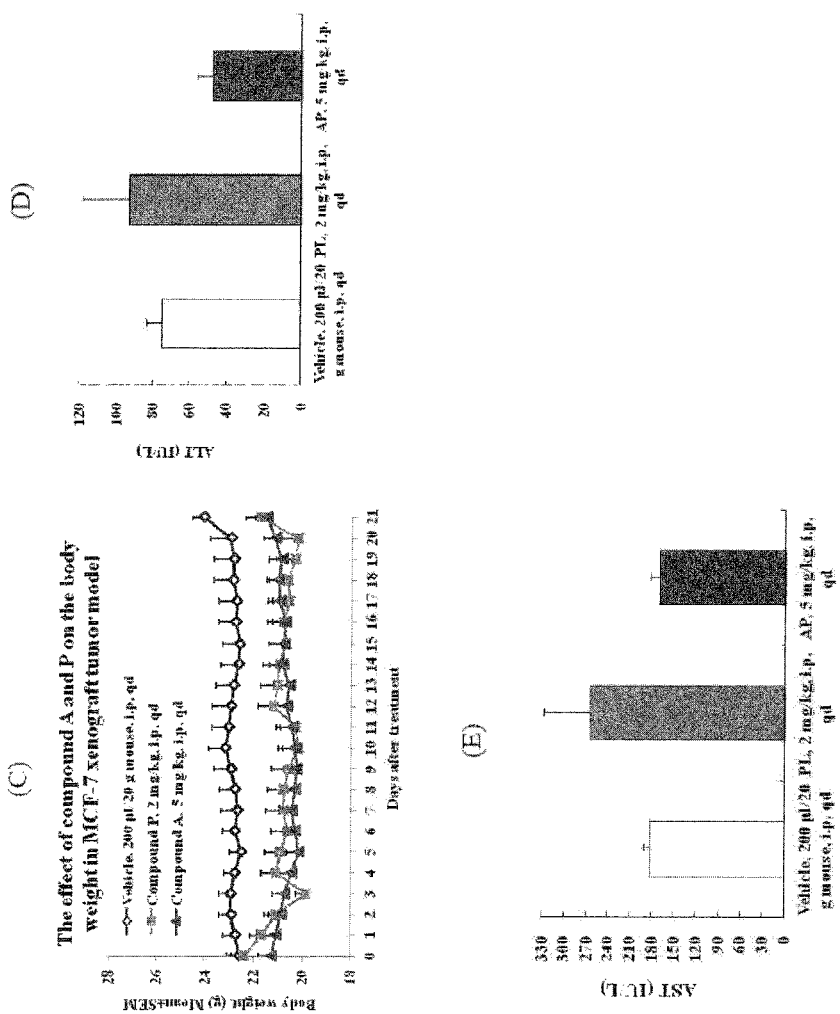

Given that PL and AP activate the intrinsic apoptotic pathway and that AP displayed selectivity for ER positive BC with low cytotoxicity to normal cells in vitro [1], we asked whether AP has similar effects in vivo. MCF-7 tumors grown up to 300 mm3 in four nude mice were harvested, dissected into 1-2 mm3 fragments and implanted into the study group for further testing. Nude mice (with tumor volume of 150 mm3) were treated with 25% Polyethylene glycol (PEG) 400 as vehicle, 2 mg/kg PL and 5 mg/kg AP for 21 days during which tumor volume, body weight and, at the time of sacrifice, tumor weight was measured. Initially mice were treated with 5 mg/kg PL however within four to six days of treatment 8 mice succumbed to treatment due to toxicity hence the well-tolerated PL dose of 2 mg/kg was used (data not shown). Although 2 mg/kg PL reduced tumor volume by approximately 17%, no difference was observed for tumor weight in comparison to vehicle (FIG. 3A). Treatment with 5 mg/kg AP for 21 days inhibited tumor growth by 45% and reduced tumor volume by 37% and in nude mice (FIGS. 3A and B). None of the animals of vehicle group exhibited tumor regression. All 5 animals in vehicle and AP treated group survived whereas one mouse died in PL treated group even at 2 mg/kg dose. The body weight of mice treated with vehicle and AP remained unaffected by treatment however mice treated with PL loss 2.5 g (12%) of body weight within the first 3 days which recovered slightly and remained stable with time (FIG. 3C). When liver tissue is damaged or inflamed liver cells tend to leak enzymes into the blood. Elevated activity of Alanine transaminase (ALT) and Aspartate transaminase (AST) liver enzyme markers in serum or blood is indicative of stress and toxicity. PL treatment increased activity of AST and ALT enzymes in mice (FIGS. 3D and E). On the contrary, AP treatment reduced the ALT and AST activity by 36% and 7%, respectively.

Example 3

PL and AP Disrupt Lipid Rafts and Deplete MCF-7 Cells of Cholesterol

Cholesterol plays an integral role in the formation of lipid rafts, steroid hormone synthesis and cell membrane formation [2,3]. Published data suggests a link between cholesterol levels and cancer where elevated cholesterol levels have been observed before and around the time of breast cancer diagnosis [4,5,6]. Cancer cells have a greater affinity for cholesterol to pace with demands of proliferation and synthesis of new membranes and lipid rafts. Pathway predictions derived from microarray expression data pointed at the impairment of cholesterol related processes by AP. To confirm whether cholesterol related pathways were affected by PL or AP, we performed lipid raft staining in MCF-7 cells and cholesterol quantitation in both MCF-7 cells and plasma samples obtained from mice. Lipid rafts of MCF-7 cells were stained using a conjugate of cholera toxin subunit B (CT-B) which binds to the pentasaccharide chain of ganglioside GM1 present in plasma membrane that selectively partitions into lipid rafts [7,8].

Figure 4:
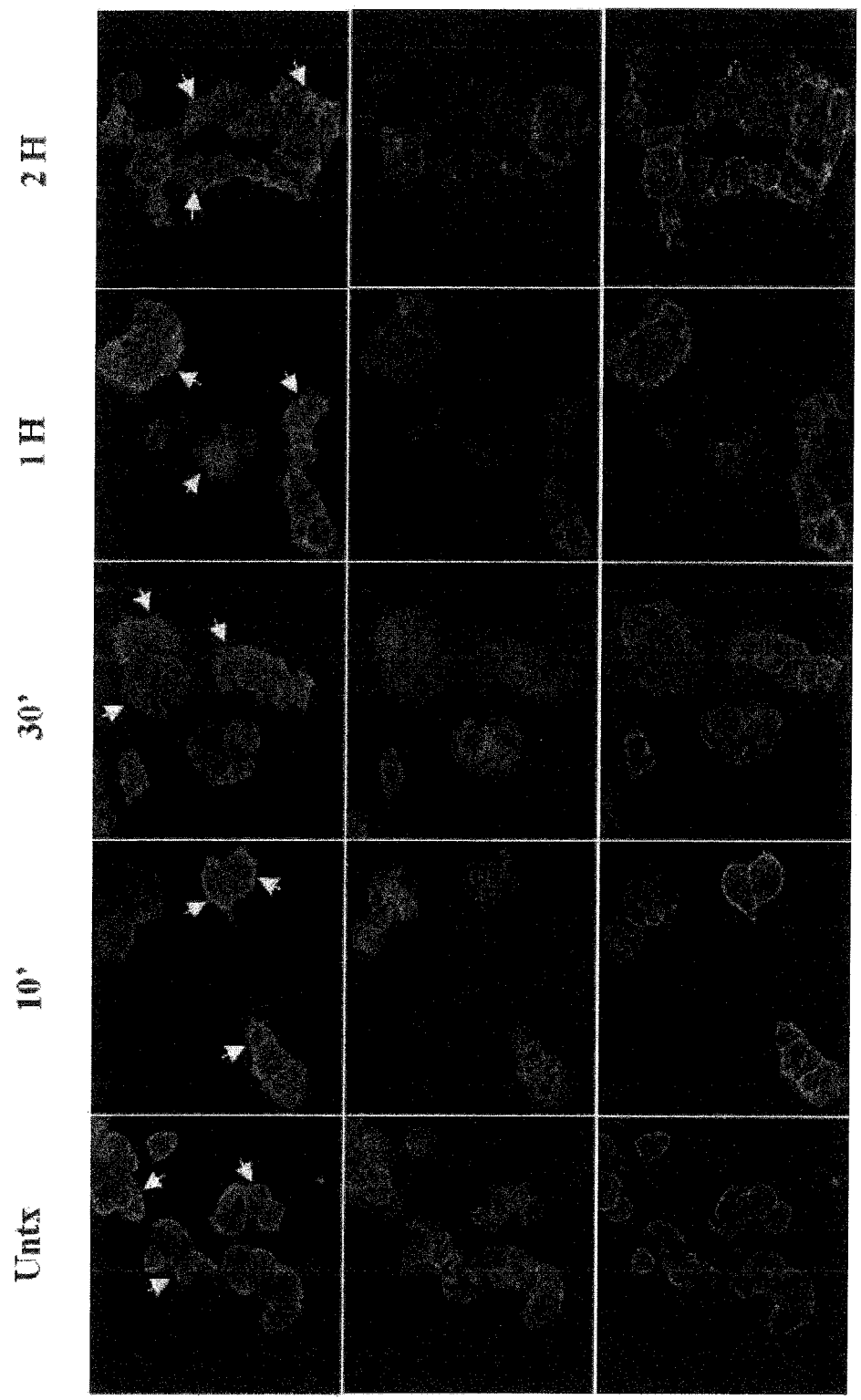
FIG. 4: Lipid raft GM1 staining in MCF-7 cells with the Vybrant® Alexa Fluor® 488 Lipid Raft Labeling Kit. Cells were cultured in 96-well plates and stained with CT-B Alexa 488 in untreated cells, and after treatment with 10 µM PL or AP for 10 min, 30 min, 1 h and 2 h.

A distinct membrane staining representing lipid rafts was observed in untreated cells however in the presence of 10 µM PL or AP over time the distribution of lipid rafts (GM1 disappearance from plasma membranes) was disrupted (FIG. 4). No distinct membrane lipid raft staining was observed in BJ cells as normal cells do not accumulate cholesterol and over express lipid rafts (Data not shown). As a result no adverse effects were observed on BJ cell morphology when treated with PL or AP.

Figure 5:
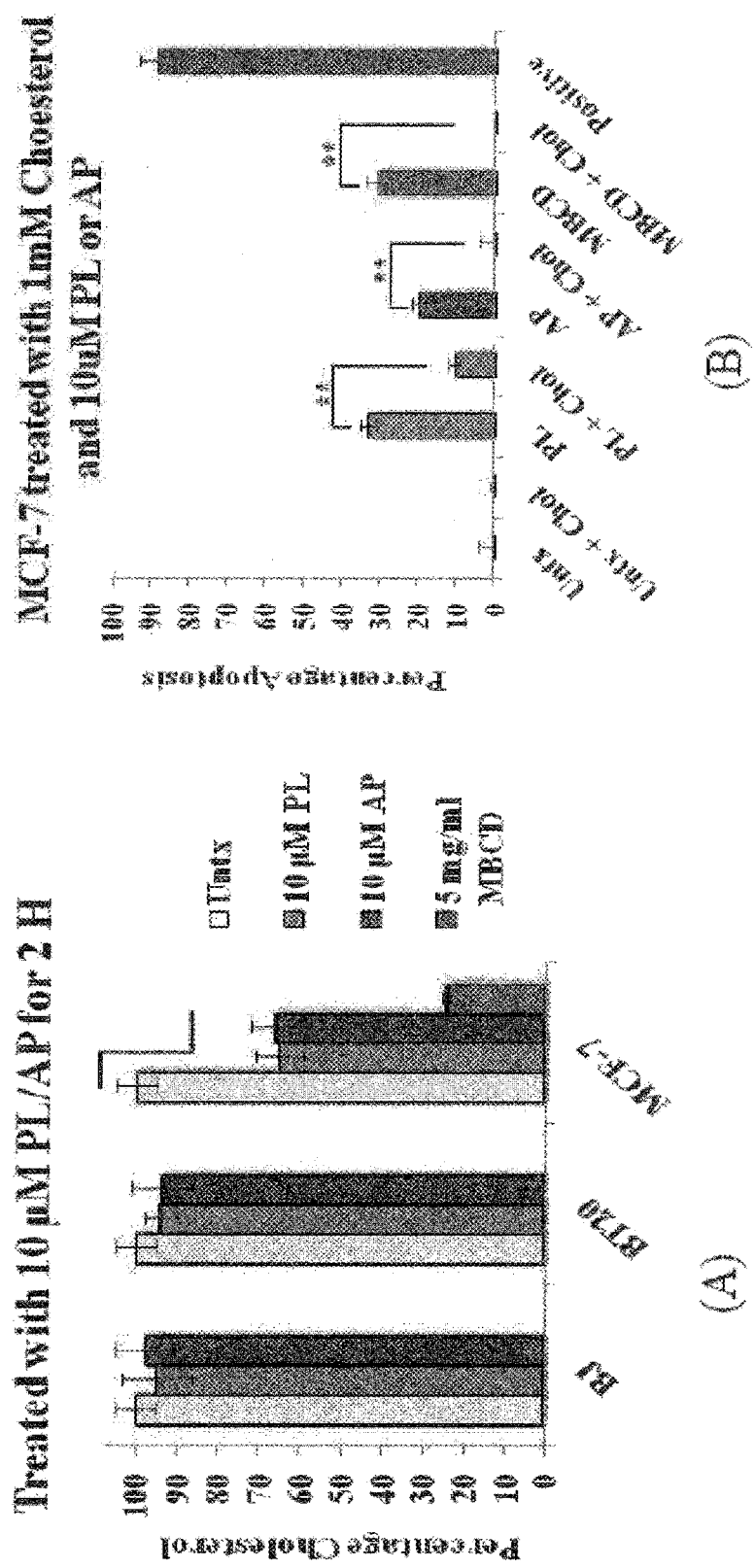
FIG. 5: Cholesterol depletion by PL and AP. BJ, BT20 and MCF-7 cells were treated with 10 µM PL or AP for 2 h and cholesterol levels were determined with the Amplex Red Cholesterol kit as per manufacturer's instructions. Cells treated with 5 mg/ml MBCD was used as a positive control and fluorescence was measured with a Tecan plate reader. MCF-7 cells were pre-incubated with 1 mM cholesterol for 1 h followed by treatment with 10 µM PL or AP for 2 h (A). Apoptosis was determined by flow cytometry with the APOPercentage kit or Cells treated with MBCD and 5 mM $H_2O_2$ served as positive controls (B). Values represent the means±SD of three independent experiments.

The redistribution and distortion of lipid rafts suggested that PL and AP interfered with cholesterol associated mechanisms. Next, we determined the effects of PL and AP on cholesterol levels in cells. Within 2 h of treatment with PL or AP, total cholesterol was reduced by 35% in MCF-7 cells as compared to untreated cells (FIG. 5). To test whether cholesterol depletion occurred in other cell types or if this was limited to ER positive BC cells, BJ and BT20 cells were also treated with PL or AP (Fig.). Treatment with 10 µM PL and AP resulted in 3-6% reduction in total cholesterol in BJ and BT20 cells relative to the untreated cells. The data thus far indicates that both PL and AP act through cholesterol modulation and that these effects might be estrogen mediated as total cholesterol in ER negative BJ and BT20 cells remained unaffected in the presence of PL or AP.

Next we asked if addition of cholesterol can rescue MCF-7 cells from undergoing apoptosis when treated with PL or AP. The addition of cholesterol significantly reduced apoptosis in PL (30% to 10%) and AP (20% to negligible) treated cells (FIG. 5B).

Example 4

PL and AP Modulate Cholesterol Levels In Vivo

Figure 6:
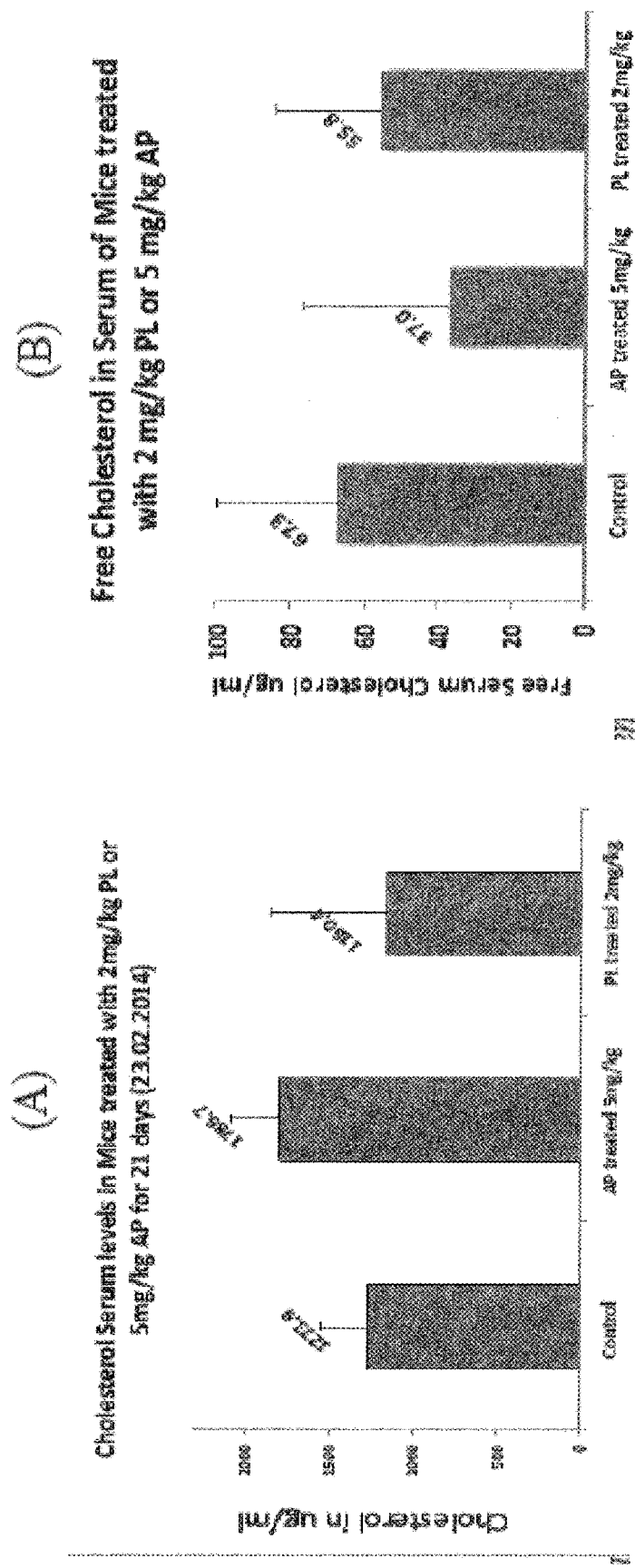
FIG. 6: Levels of total Cholesterol (A) and unbound free cholesterol (B) in mice serum after treatment with 2 mg/kg PL or 5 mg/kg AP were determined with the Amplex Red assay kit. Levels of total cholesterol, HDL and LDL/VLDL in mice serum determined with ABNOVA HDL and LDL/VLDL Assay kit (C). Values represent the means±SD of three independent experiments. Reference values have been adapted from http://www.abcam.com/hdl-and-ldlvldl-cholesterol-assay-kit-ab65390.html.

We next asked whether changes observed in cholesterol levels in vitro are also observable in vivo. Total cholesterol levels in serum of MCF-7 xenograft models were measured with the AMPLEX Red kit. Negligible alterations to total cholesterol were noted for 2 mg/kg PL treatment after 21 days when compared to Vehicle control (FIG. 6A). A significant increase in the amount of cholesterol in serum of mice treated with 5 mg/kg AP was observed which suggested cholesterol efflux/depletion from cells into the serum in the presence of AP in vivo. We then determined whether the elevated level of cholesterol noted in mice treated with AP was bound or unbound. Using the AMPLEX Red assay, but excluding the cholesterol esterase enzyme, the level of free cholesterol was determined (FIG. 6B). Although the amount of free cholesterol compared to the overall total amount of cholesterol in mice was minute, free cholesterol level in AP treated mice was significantly lower than that of the PL or control groups (FIG. 6B).

The balance between the HDL and LDL ratio has important physiological implications. Excess cholesterol is cleared up from the bloodstream by HDL by reverse cholesterol transport (RCT). HDL also maintains cellular cholesterol homeostasis by unloading excess cholesterol from cells [9]. Not surprisingly an imbalance in HDL:VLDL/LDL levels has been correlated with the progression of atherosclerosis [10]. A different kit (ABNOVA HDL and VLDL assay kit) and spectrophotomical measurements were employed to determine the levels of total, HDL and LDLNLDL cholesterol. Serum samples of mice were separated into different fractions as per manufacturer's instructions (FIG. 6C). The ratio of HDL to LDLNLDL in Vehicle group was 3.4:1. In the AP treated group total cholesterol levels were also elevated as observed earlier however the ratio of HDL to LDLNLDL (3.1:1) remained similar to that of Vehicle group. On the contrary PL treated mice, with slightly lower total cholesterol compared to the Vehicle group, had a ratio of HDL to LDLNLDL of 1.8:1. Our data so far suggests that although both PL and AP possess cholesterol modulating effects in vitro and in vivo AP is safer to use as it maintains the HDL:LDL/VLDL balance.

Example 5

Cholesterol Ester Transfer Protein (CETP): A New Link to Cancer

CETP transfers cholesterol esters and triglycerides between plasma lipoproteins and plays an important role in the RCT i.e. transport of cholesterol to the liver for excretion in order to maintain cholesterol homeostasis [11]. In the past decade, it was believed that CETP inhibition results in increased HDL levels and reduce the occurrence of cardiovascular disease (CVD) [12], which led to several clinical trials to test the anti-atherosclerosis effects of CETP inhibition. Alternatively, it is also reported that CETP also facilitates efflux of cellular free cholesterol and an increase in plasma CETP activity is linked to an enhanced capacity of plasma to promote cholesterol efflux from human macrophages independent of lipid variations [13]. Recently, it has been proposed based on extensive published data that CETP inhibition does not test the increase in HDL hypothesis as hoped, and CETP has a protective effect by accelerating RCT [14]. This controversial role of CETP calls for more detailed investigations in cholesterol related diseases.

Several experimental and clinical studies have also linked the cholesterol [15,16,17], cholesterol metabolites [5,18] and lipoproteins [4,19] to carcinogenesis and tumor development. Since CETP maintains cholesterol homeostasis, we hypothesized that CETP might be fueling the cancer cells by maintaining the cholesterol supply for rapid cell growth and division. Therefore, understanding the role of CETP in cancer is important.

Figure 7:
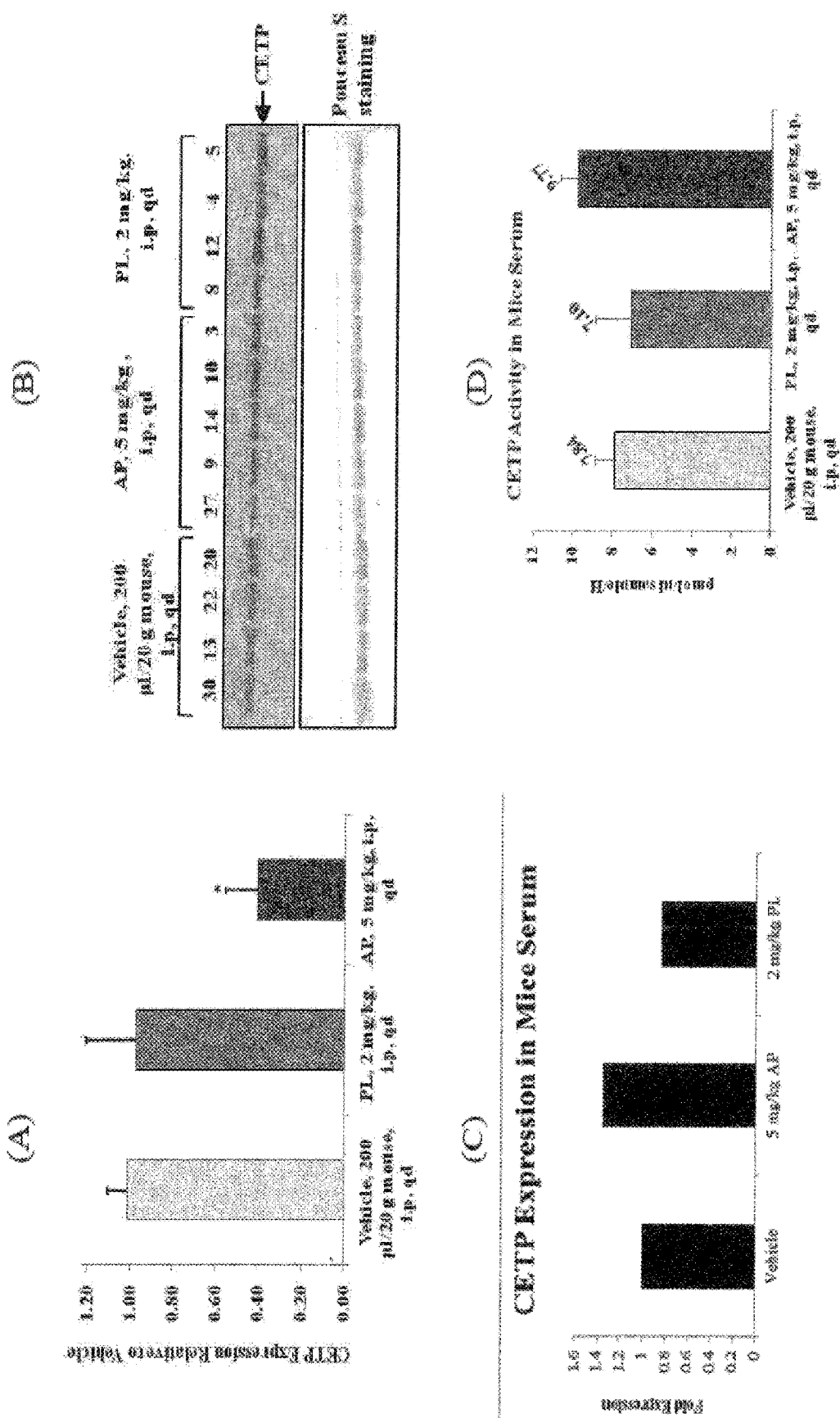
FIG. 7: Levels of CETP mRNA in tumor (A) and protein in serum (B) in mice tumor samples after treatment with 2 mg/kg PL or 5 mg/kg AP were determined with the RT-PCR and western blotting, respectively. Fold change in expression of serum protein was determined using densitometry analysis of western blots using ImageJ (C). CETP activity in serum was estimated using CETP activity kit (name of kit/manufacturer) (D). Values represent the means±SD of three independent experiments. * where $p \leq 0.05$, and ** where $p \leq 0.005$.

We performed qRT-PCR using mRNA isolated from mice tumor samples to determine the expression of CETP after treatment with PL and AP (FIG. 7A). Notably, AP treatment significantly reduced the expression of CETP in tumors by 60%, however, PL had no effect on CETP transcription. CETP mRNA is translated into 74 kD protein comprised of 476 amino acids that localizes in plasma [11]. The nude mice used in this study were CETP null/deficient hence any CETP levels in serum would reflect that emanating from the tumors. CETP protein levels in mice serum samples were determined by western blotting (FIG. 7B). Densitometry analysis of CETP protein levels revealed that AP upregulated CETP levels while CETP levels were slightly reduced in the PL treated group when compared to Vehicle (Data not shown).

The activity of CETP in mice plasma was determined using the CETP activity assay kit according to the manufacturer's instructions (FIG. 7D). CETP activity was elevated in AP treated mice compared to Vehicle. This observation was in accordance with the CETP protein expression levels observed in Vehicle, AP and PL test groups. The expression levels of CETP have been reported to be linear with its activity [14].

Example 6

CETP Helps to Maintain Cellular Cholesterol Levels in Cancer Cells

Figure 8:
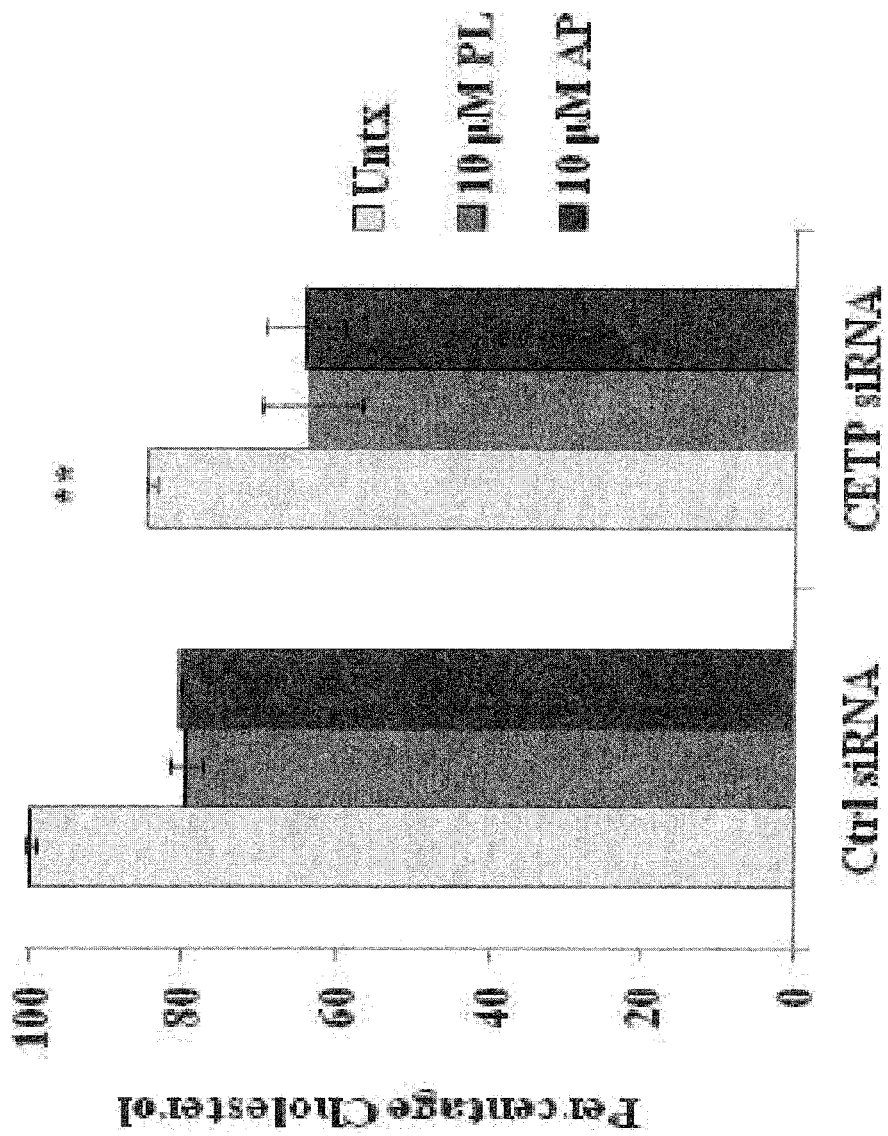
FIG. 8: Levels of total cholesterol in MCF-7 control (cntl) siRNA and CETP knock-out cells after treatment with 10 µM PL or AP were determined with the Amplex Red assay kit. Values represent the means±SD of three independent experiments.

The in vivo data suggested that AP modulates CETP levels and activity. Since we could only capture the protein expression and activity of CETP in mice serum which did not reflect the effects of CETP ablation in tumor cells, we studied the role of CETP in MCF-7 cells in vitro. Transient transfection of MCF-7 cells with siRNA directed to CETP resulted in an 80% or greater inhibition of CETP mRNA (data not shown). We measured the amount of cholesterol in CETP knock-out MCF-7 untreated and/or treated with 10 μM AP and PL. The total cholesterol was decreased in untreated CETP siRNA cells by 11%, however AP and PL treated knock-out cells did not show results any different from control (ctrl) siRNA cells. (FIG. 8). This demonstrates that knocking-out CETP in optimally growing MCF-7 leads to lowered cholesterol levels in these cells. No significant changes were observed in cholesterol levels of BJ CETP siRNA cells whether treated with PL or AP or left untreated (data not shown).

Example 7

CETP is Required for Growth of Cancer Cells

Figure 9:
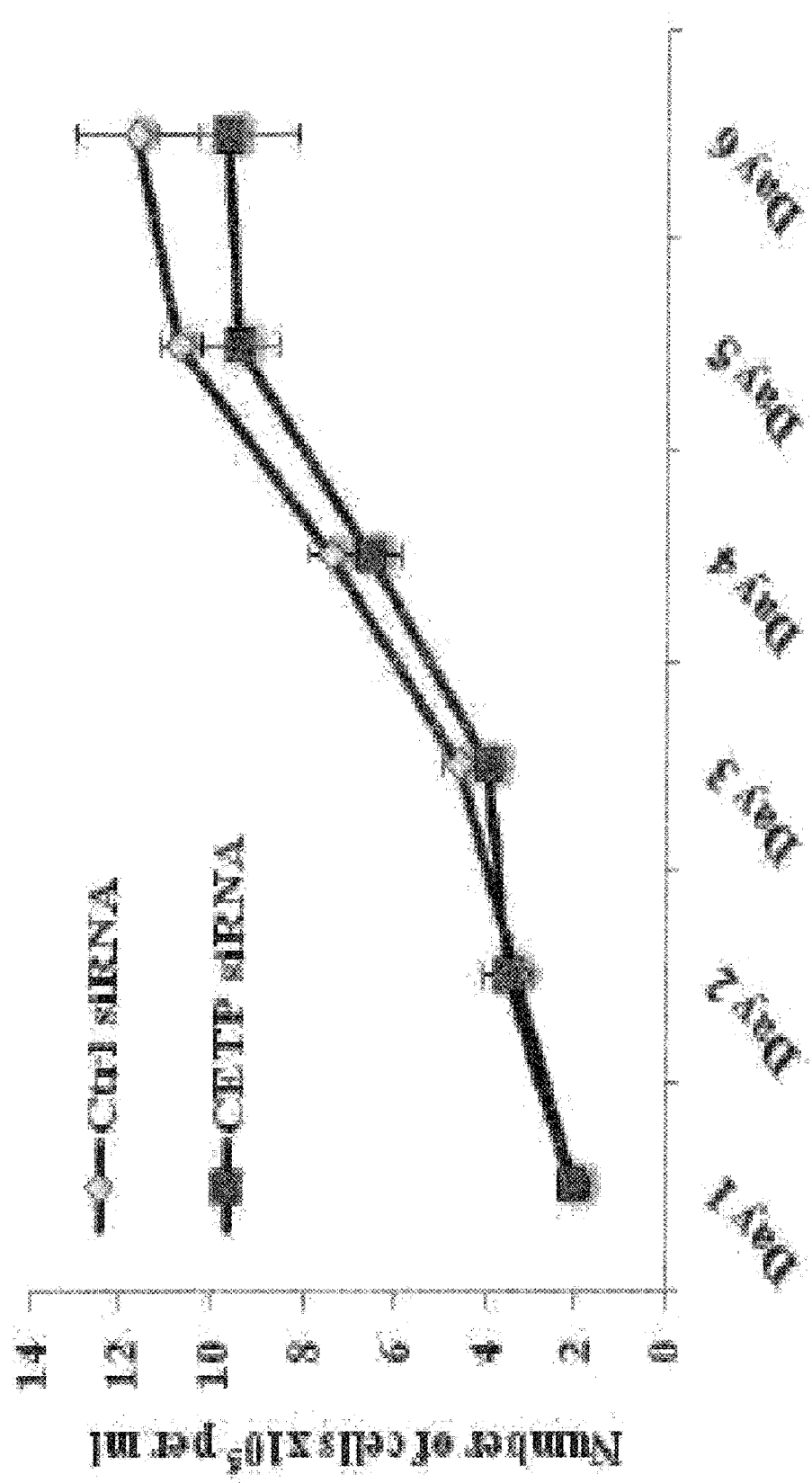
FIG. 9: The effect of CETP mRNA silencing on proliferation of MCF-7 cells was measured by counting cells with a Countess cell counter (Invitrogen) over a period of six days. Values represent the means±SD of three independent experiments.

We investigated whether CETP is required for optimal growth of cancer cells. We silenced the CETP gene in MCF-7 cells and measured their growth over a period of six days. Interestingly, the proliferation of MCF-7 cells was reduced by 20% (FIG. 9).

Example 8

CETP Acts as an Anti-Apoptotic Gene in Cancer Cells

Since, as shown above, CETP is required for optimal growth of MCF-7 cells, we further hypothesized that CETP may help cancer cell to resist/escape apoptotic signals thus preventing cell death. Several apoptotic markers such as MOMP, phosphatidylserine exposure and caspase-3/7 activity were tested to establish a link between CETP and apoptosis.

Figure 10:
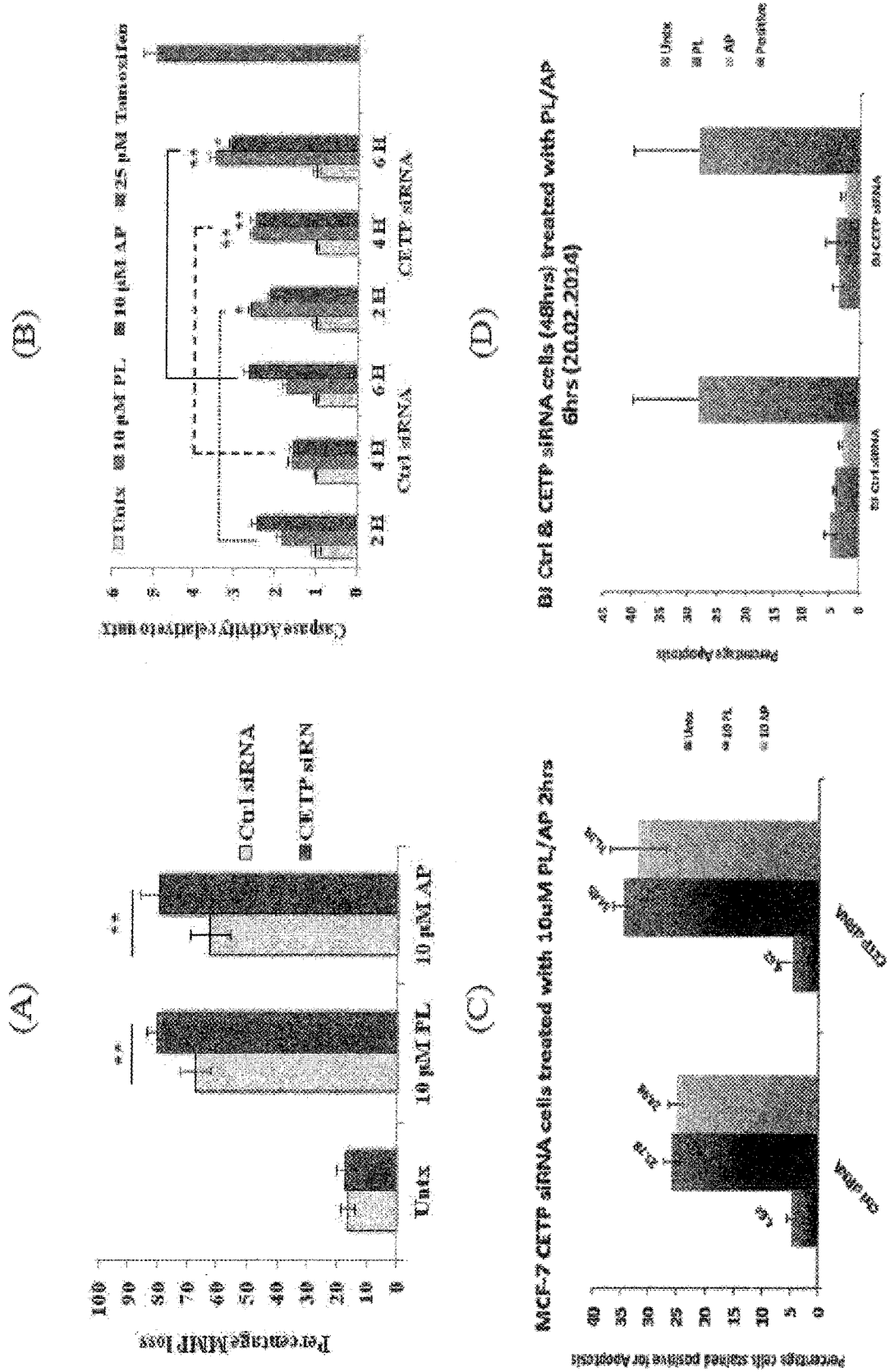
FIG. 10: The effect of CETP mRNA silencing on MMP (A), Capase-3/7 activity (B) and apoptosis in MCF-7 (C) and BJ (D) untransfected, cntl siRNA and CETP knockout cells after treatment with 10 µM PL or AP. Values represent the means±SD of three independent experiments.
Figure 11:
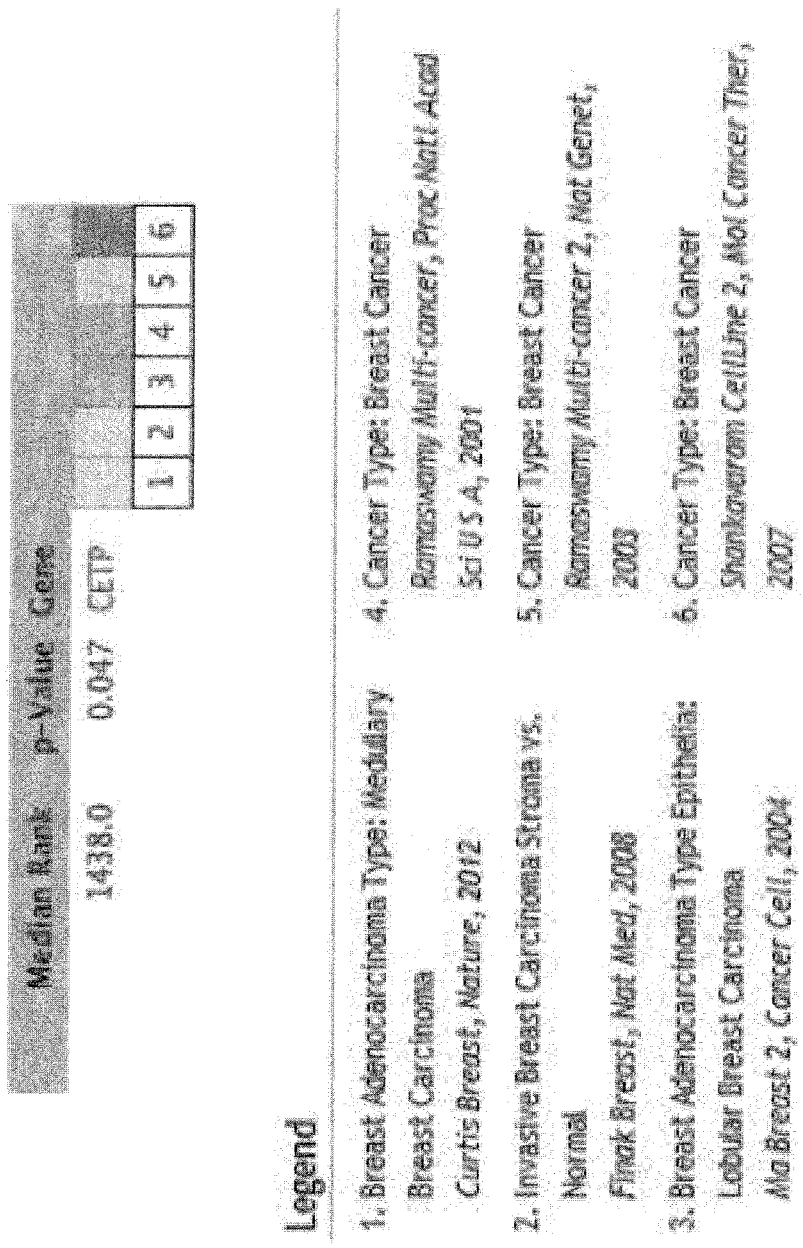
FIG. 11: Over-expression of CETP mRNA in six published breast cancer microarray datasets available in Oncomine (website: oncomine.org).

CETP knockdown alone had no observable effects on MMP, however, in the presence of PL or AP a reduction in MMP of 13 and 17% respectively was observed when compared to Ctrl siRNA cells (FIG. 10A). Next, we intended to see if CETP silencing increased sensitivity of MCF-7 cells to apoptosis. In the presence of PL or AP, CETP knockdown significantly increased the caspases-3/7 activity in MCF-7 cells (FIG. 10B). Finally, the level of apoptosis in MCF-7 CETP siRNA cells was found to be increased by 10% in the presence of PL or AP (FIG. 10C), whereas no increased sensitivity to apoptosis was observed in BJ CETP knockdown cells treated with PL or AP (FIG. 10D).

Our data suggests that CETP plays a role in cancer cell survival and cholesterol metabolism as knockdown of CETP resulted in an increased sensitivity to apoptosis and a decrease in total cholesterol. Although CETP is secreted into the extracellular environment and bloodstream/plasma we propose that CETP expression locally plays a role in cell growth and apoptosis. To get an idea about the mRNA expression levels of CETP in breast cancer, we compared the expression of CETP mRNA (as compared to normal) in six published microarray datasets in Oncomine. CETP mRNA was over-expressed in these datasets (FIG. 1). Our results suggest a link between cholesterol, CETP and breast cancer.

Example 9

Effect of CETP Knockout on Tamoxifen Action in MCF-7 Cells

Figure 12:
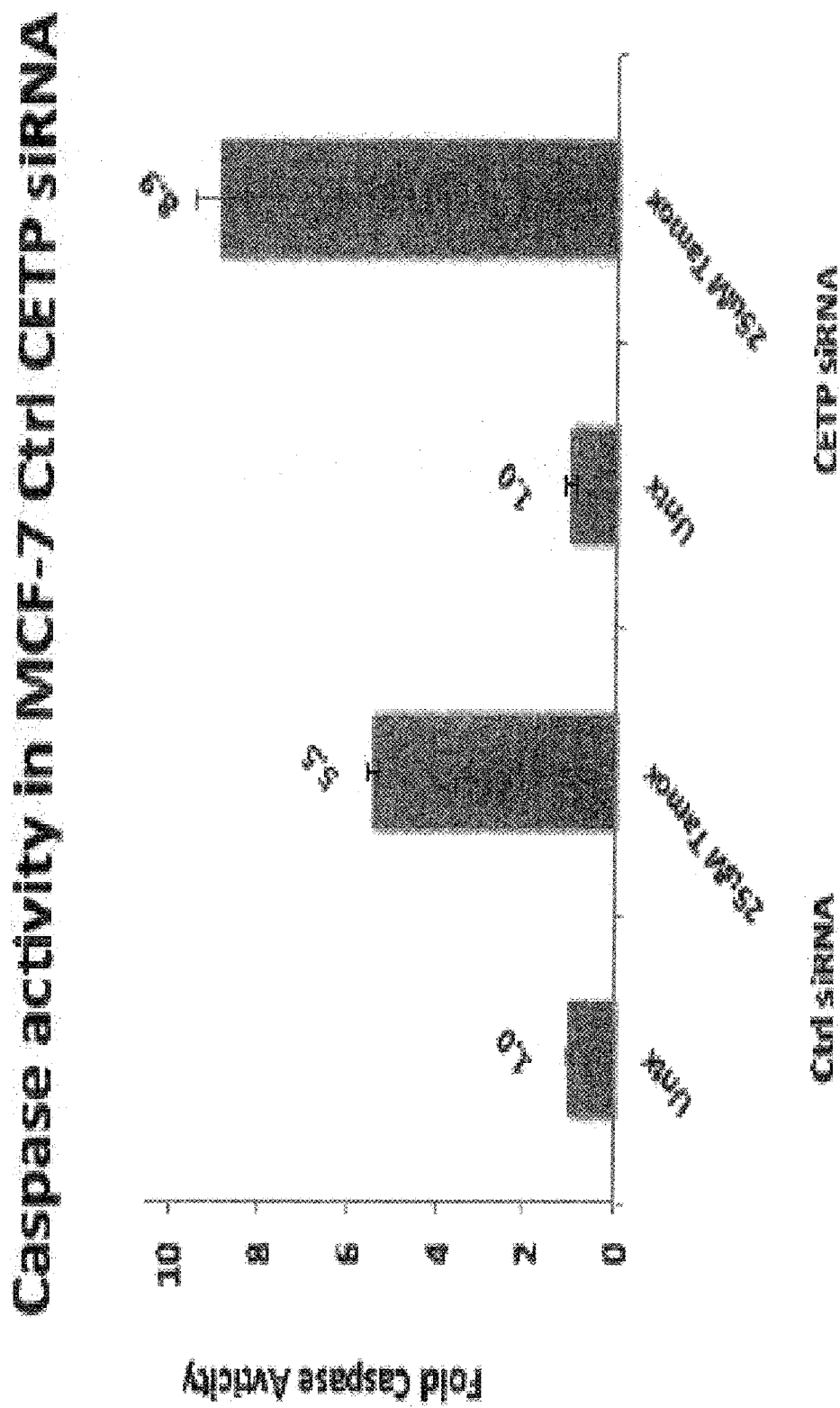
FIG. 12: The effect of CETP mRNA knockout on Capase-3/7 activity (A) and apoptosis (B) in MCF-7 cntl siRNA and CETP knockout cells after treatment with 25 µM tamoxifen for 24 h. Values represent the means±SD of three independent experiments.

To test if effect of CETP knockout on apoptosis in MCF-7 is limited to AP, we treated the CETP knockout MCF-7 cells with tamoxifen (a known first line drug for breast cancer treatment). A significant increase in caspase-3/7 activity was observed (FIG. 12). This observation was not limited to PL and AP as similar observations were made in CETP knockdown cells treated with tamoxifen (FIG. 12).

Example 10

AP Reduce Toxicity and Increase Efficacy of Known Chemotherapeutic Drugs

Figure 13:
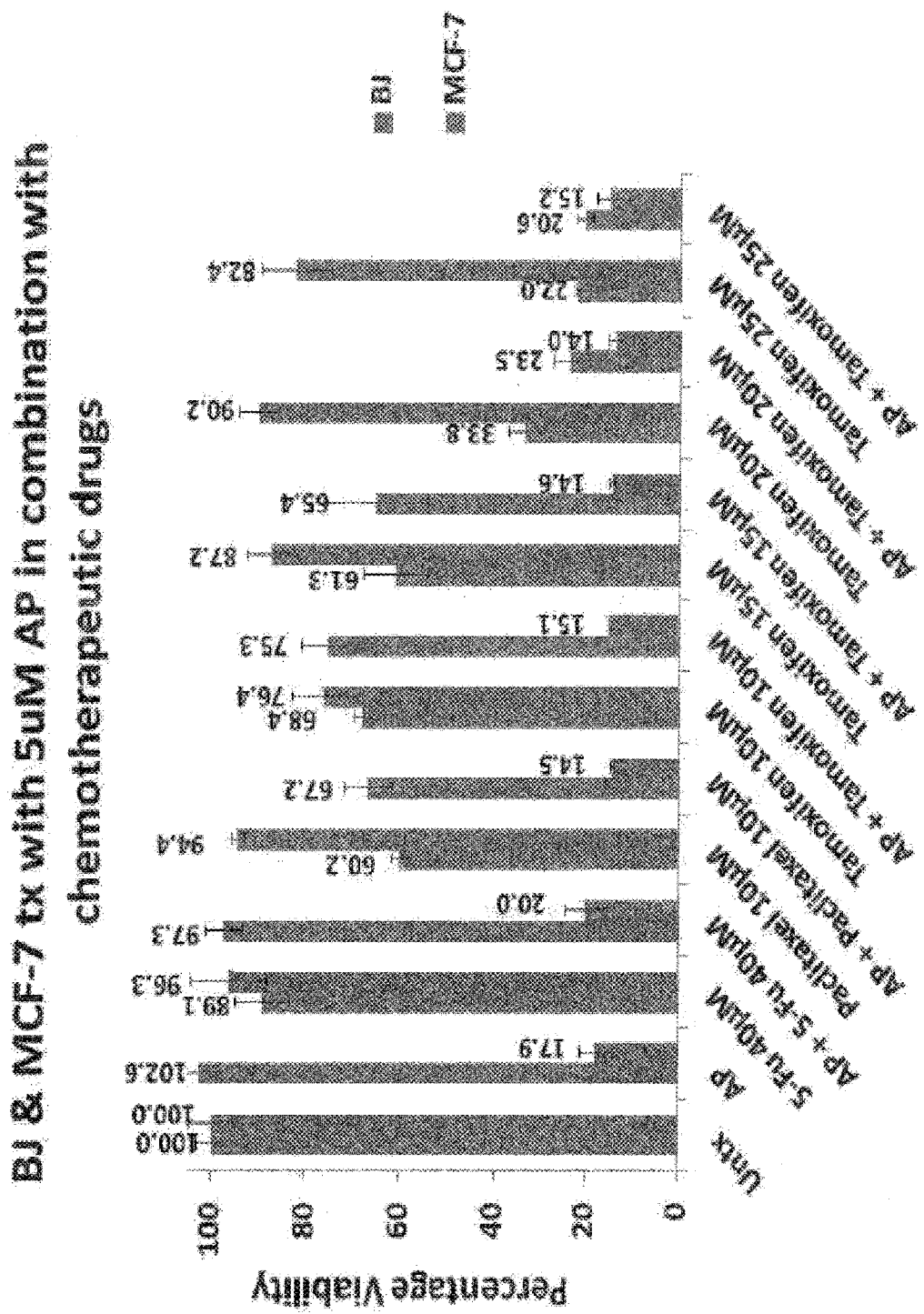
FIG. 13: The effect of AP on viability of BJ and MCF-7 cells when combined with different doses of various chemotherapeutic drugs for 24 h. Values represent the means±SD of three replicates.

In our earlier in vivo experiments, we found that AP could even reduce the toxicity linked with vehicle control as demonstrated by ALT and AST levels. We anticipated that AP might have the potential to reduce toxicity and increase efficacy of known chemotherapeutic drugs which may enhance the usage of these drugs at lower concentrations with increased cancer killing effects. To test this preliminary, we treated normal (BJ) and Cancer (MCF-7) cells with different chemotherapeutic drugs as summarized in FIG. 13.

The results of this experiment show that AP when used in combination with 5-Florouracil increases cell viability of normal cells (7%) while at the same time reduces viability of cancer cells (76%). Similar effects were noticed in the case of paclitaxel. Various concentrations of Tamoxifen were tested and it was found that AP was unable to rescue normal cells from toxic effects of tamoxifen at higher concentrations but when used with 10 μM of tamoxifen, the viability of normal cells was increased by 7% and viability of cancer cells was reduced by 50%. It is also clear from data that the cancer killing effect achieved using 20 μM tamoxifen was possible to achieve using a combination of AP with 10 μM tamoxifen while enhancing the viability of normal cells at the same time.

This preliminary data shows that the AP combined with half the dose of tamoxifen can help to achieve long term benefits in terms of reduced toxicity and enhanced efficacy.

Example 11

CETP: A Target of AP (Evidence that AP Binds to CETP Inside the Cells)

Figure 14:
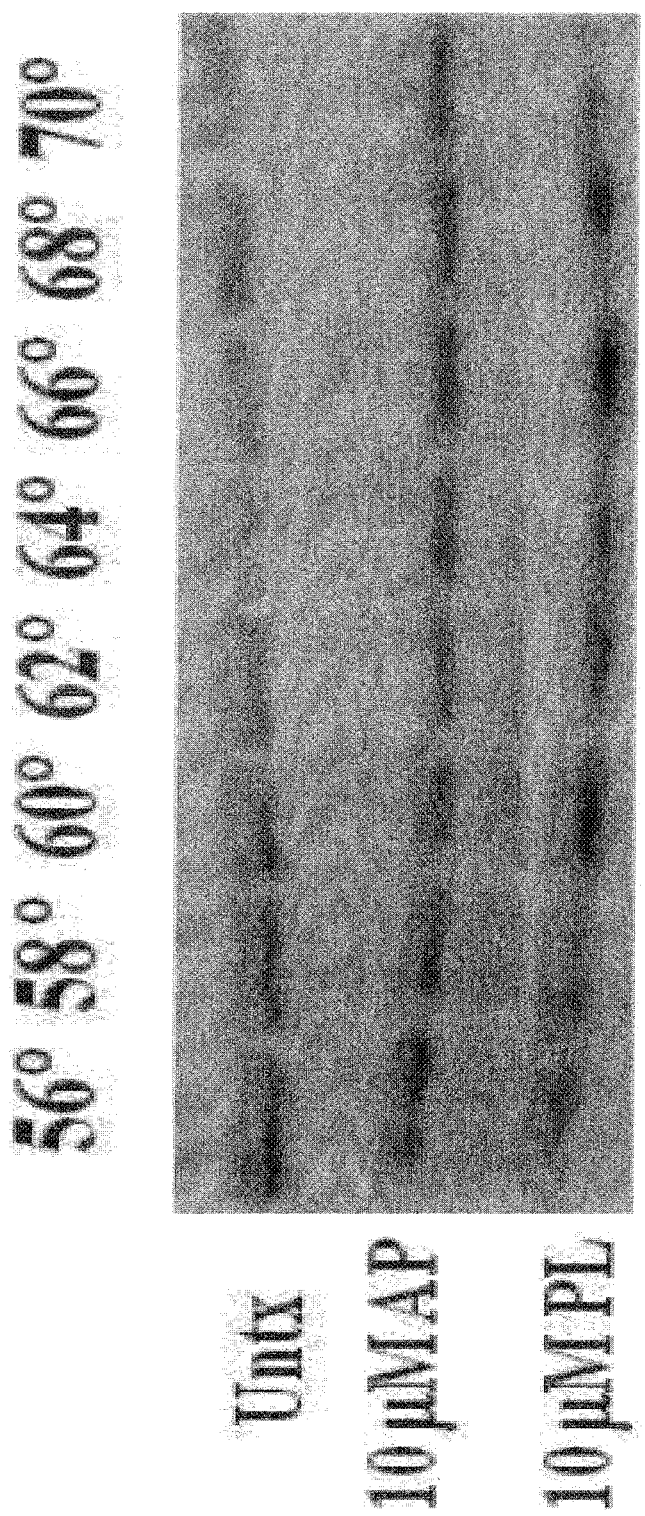
FIG. 14: Illustration of the amount of stabilized CETP protein in the presence of compounds using TSA. MCF-7 cells were left untreated (Untx) and were treated with 10 µM of AP/PL for two hours. TSA was performed using temperature range 56° C. to 70° C. with 2° C. intervals. The western blotting was performed after the assay and CETP was detected. The experiment was performed in duplicate.

Thermal shift assay (TSA) captures the drug protein binding using the fact that the thermostability of the protein is changed after ligand binding. We did three runs of TSA [20] to identify direct binding of AP with CETP (FIG. 14). The data shows that in untreated MCF-7 cells, the level of protein starts decreasing around 64° C. while CETP seems to be more stable even at 70° C. in cells treated with 10 µM of AP/PL. These results confirm that AP binds to CETP in the cells. Further studies are needed to study the effects of thermostability on function of CETP.

CONCLUSIONS

The following can be concluded from the experimental results described above:
1. AP has the potential to kill estrogen positive breast cancer cells both in vivo and in vitro at dose which is not toxic to normal cells.
2. AP kills cancer cells by depleting cholesterol from membranes of cholesterol enriched cancer cells that triggers cell death pathways. This is confirmed as replenishing cholesterol blocks cell death.
3. Depleted cholesterol comes to plasma for clearance. AP maintains HDL/LDL ratio for optimal clearance of cholesterol.
4. AP increases CETP activity (this activity is inversely related to cardiovascular diseases) leading to clearance of excess cholesterol from plasma to liver.
5. Discovered link of CETP to cancer (new cancer biology—never reported before).
6. Knocking-out CETP slowed growth of cultured cancer cells by 20% within 6 days.
7. CETP knockout also modulated cell death signaling pathways (apoptosis).
8. CETP also increased caspases-3/7 activity (these enzymes are executioners of apoptotic cell death) linked to Tamoxifen (this drug is a gold standard breast cancer therapy).
9. AP binds to CETP inside the MCF-7 cancer cells.
10. AP when combined with Tamoxifen, increased the viability of normal cells and significantly decreased the viability of cancer cells. It means AP protects normal cells from toxic effects of Tamoxifen and helps Tamoxifen to kill cancer cells at half of its dose.
11. Overall, we identified a molecule that has following advantageous characteristics: anticancer activity; anti-atherosclerosis activity; and utility as an adjunct therapy to reduce toxicity and increase efficacy of currently used chemotherapeutic drugs.

REFERENCES

1. Sagar, S.; Esau, L.; Moosa, B.; Khashab, N. M.; Bajic, V. B.; Kaur, M. Cytotoxicity and apoptosis induced by a plumbagin derivative in estrogen positive MCF-7 breast cancer cells. *Anti-cancer agents in medicinal chemistry* 2014, 14, 170-180.
2. Cruz, P. M.; Mo, H.; McConathy, W. J.; Sabnis, N.; Lacko, A. G. The role of cholesterol metabolism and cholesterol transport in carcinogenesis: a review of scientific findings, relevant to future cancer therapeutics. *Frontiers in pharmacology* 2013, 4, 119.
3. Gorin, A.; Gabitova, L.; Astsaturov, I. Regulation of cholesterol biosynthesis and cancer signaling. *Current opinion in pharmacology* 2012, 12, 710-716.
4. dos Santos, C. R.; Domingues, G.; Matias, I.; Matos, J.; Fonseca, I.; de Almeida, J. M.; Dias, S. LDL-cholesterol signaling induces breast cancer proliferation and invasion. *Lipids in health and disease* 2014, 13, 16.
5. Kaiser, J. Cancer. Cholesterol forges link between obesity and breast cancer. *Science* (New York, N.Y.) 2013, 342, 1028.
6. Llanos, A. A.; Makambi, K. H.; Tucker, C. A.; Wallington, S. F.; Shields, P. G.; Adams-Campbell, L. L. Cholesterol, lipoproteins, and breast cancer risk in African American women. *Ethnicity & disease* 2012, 22, 281-287.
7. Janes, P. W.; Ley, S. C.; Magee, A. I. Aggregation of lipid rafts accompanies signaling via the T cell antigen receptor. *The Journal of cell biology* 1999, 147, 447-461.
8. Merritt, E. A.; Sixma, T. K.; Kalk, K. H.; van Zanten, B. A.; Hol, W. G. Galactose-binding site in *Escherichia coli* heat-labile enterotoxin (LT) and cholera toxin (CT). *Molecular microbiology* 1994, 13, 745-753.
9. Lewis, G. F.; Rader, D. J. New insights into the regulation of HDL metabolism and reverse cholesterol transport. *Circulation research* 2005, 96, 1221-1232.
10. Hao, W.; Friedman, A. The LDL-HDL profile determines the risk of atherosclerosis: a mathematical model. *PloS one* 2014, 9, e90497.
11. Le Goff, W.; Guerin, M.; Chapman, M. J. Pharmacological modulation of cholesteryl ester transfer protein, a new therapeutic target in atherogenic dyslipidemia. *Pharmacology & therapeutics* 2004, 101, 17-38.
12. Tchoua, U.; D'Souza, W.; Mukhamedova, N.; Blum, D.; Niesor, E.; Mizrahi, J.; Maugeais, C.; Sviridov, D. The effect of cholesteryl ester transfer protein overexpression and inhibition on reverse cholesterol transport. *Cardiovascular research* 2008, 77, 732-739.
13. Villard, E. F.; El Khoury, P.; Duchene, E.; Bonnefont-Rousselot, D.; Clement, K.; Bruckert, E.; Bittar, R.; Le Goff, W.; Guerin, M. Elevated CETP activity improves plasma cholesterol efflux capacity from human macrophages in women. *Arteriosclerosis, thrombosis, and vascular biology* 2012, 32, 2341-2349.
14. Miller, N. E. CETP inhibitors and cardiovascular disease: Time to think again. *F1000Research* 2014, 3, 124.
15. Danilo, C.; Frank, P. G. Cholesterol and breast cancer development. *Current opinion in pharmacology* 2012, 12, 677-682.
16. Niendorf, A.; Nagele, H.; Gerding, D.; Meyer-Pannwitt, U.; Gebhardt, A. Increased LDL receptor mRNA expression in colon cancer is correlated with a rise in plasma cholesterol levels after curative surgery. *International journal of cancer. Journal international du cancer* 1995, 61, 461-464.
17. Solomon, K. R.; Freeman, M. R. The complex interplay between cholesterol and prostate malignancy. *The Urologic clinics of North America* 2011, 38, 243-259.
18. Nelson, E. R.; Wardell, S. E.; Jasper, J. S.; Park, S.; Suchindran, S.; Howe, M. K.; Carver, N. J.; Pillai, R. V.; Sullivan, P. M.; Sondhi, V.; Umetani, M.; Geradts, J.; McDonnell, D. P. 27-Hydroxycholesterol links hypercholesterolemia and breast cancer pathophysiology. *Science* (New York, N.Y.) 2013, 342, 1094-1098.
19. Muntoni, S.; Atzori, L.; Mereu, R.; Satta, G.; Macis, M. D.; Congia, M.; Tedde, A.; Desogus, A.; Muntoni, S. Serum lipoproteins and cancer. *Nutrition, metabolism, and cardiovascular diseases: NMCD* 2009, 19, 218-225.

20. Jafari, R.; Almqvist, H.; Axelsson, H.; Ignatushchenko, M.; Lundback, T.; Nordlund, P.; Martinez Molina, D. The cellular thermal shift assay for evaluating drug target interactions in cells. *Nature protocols* 2014, 9, 2100-2122.

What is claimed is:

1. A method of reducing cancer cell growth in cancer patient in need thereof comprising administering to the patient an agent effective to inhibit Cholesteryl Ester Transfer Protein (CETP) in cancer cells,
   wherein the at least one Cholesteryl Ester Transfer Protein (CETP) inhibitor is an SiRNA specific for CETP or a compound selected from the group consisting of dalceptrpib, anacetrapib, evacetrapib, torcetrapib, and atorvastatin,
   wherein the cancer is selected from the group consisting of breast cancer and colon cancer.

2. The method of claim 1, wherein the cancer is breast cancer.

3. The method of claim 1, wherein the CETP inhibitor is administered in combination with one or more additional anticancer agents.

4. The method of claim 1, wherein the breast cancer is estrogen positive breast cancer.

5. The method of claim 3, wherein the one or more additional anticancer agents is selected from the group consisting of tamoxifen, paclitaxel, and fluorouracil.

6. The method of claim 2, wherein the breast cancer is refractory breast cancer.

7. The method of claim 6, wherein the patient has developed an acquired anti-estrogen resistance.

8. The method of claim 2, wherein the subject exhibits an intrinsic resistance to anti-estrogen and anti-HER2 therapies.

9. The method according to claim 1, wherein the CETP inhibitor is a CETP siRNA or torcetrapib.

* * * * *